(12) United States Patent
Shi et al.

(10) Patent No.: US 11,420,987 B2
(45) Date of Patent: Aug. 23, 2022

(54) TRIARYL PHOSPHINE LIGANDS, PREPARATION METHOD THEREFOR, AND USE IN CATALYSING COUPLING REACTIONS

(71) Applicant: DONGGUAN STEPHEN CATALYST CO., LTD., Guangdong (CN)

(72) Inventors: Jicheng Shi, Guangdong (CN); Fabin Zhou, Guangdong (CN)

(73) Assignee: DONGGUAN STEPHEN CATALYST CO., LTD., Guangdong (CN)

( * ) Notice: Subject to any disclaimer, the term of this patent is extended or adjusted under 35 U.S.C. 154(b) by 0 days.

(21) Appl. No.: 16/977,390

(22) PCT Filed: Mar. 28, 2019

(86) PCT No.: PCT/CN2019/079966
§ 371 (c)(1),
(2) Date: Dec. 24, 2020

(87) PCT Pub. No.: WO2019/170163
PCT Pub. Date: Sep. 12, 2019

(65) Prior Publication Data
US 2021/0147452 A1    May 20, 2021

(30) Foreign Application Priority Data
Mar. 7, 2018    (CN) .......................... 201810187687.2

(51) Int. Cl.
*B01J 31/00*    (2006.01)
*C07F 9/50*    (2006.01)
*B01J 31/24*    (2006.01)
*C07F 15/00*    (2006.01)
*C07F 15/04*    (2006.01)

(52) U.S. Cl.
CPC .......... *C07F 9/5022* (2013.01); *B01J 31/2404* (2013.01); *C07F 15/006* (2013.01); *C07F 15/04* (2013.01)

(58) Field of Classification Search
None
See application file for complete search history.

(56) References Cited

FOREIGN PATENT DOCUMENTS

CN        105859774 A        8/2016

OTHER PUBLICATIONS

Smith, Rhett, et al., "Suzuki reactions catalyzed by palladium complexes bearing the bulky (2,6-dimesitylphenyl) dimethylphosphine", Tetrahedron Letters, (Sep. 28, 2004), Tetrahedron Letters 45 (2004), pp. 8327-8330.
Ortega-Moreno, Laura, et al., "Synthesis, Properties, and Some Rhodium, Iridium, and Platinum Complexes of a Series of Bulky m-Terphenylphosphine Ligands", Polyhedron: The International Journal for Research in Inoganic Chemistry, (2016), 25 pages.
Buster, Bryan, et al., "m-Terphenylphosphines: Synthesis, structures and coordination properties", Inorganica Chimica Acta 362, Journal homepage: www.elsevier.com/locate/ica, (2009), Elsevier B.V., pp. 3465-3674.

*Primary Examiner* — Yun Qian
(74) *Attorney, Agent, or Firm* — Muncy, Geissler, Olds & Lowe, P.C.

(57) ABSTRACT

Provided are triaryl phosphine ligands, as shown in general formulae Ia and Ib, or a mixture thereof, and a preparation method therefor. The invention addresses the deficiencies of biaryl phosphine ligands invented by Buchwald et al. Also provided are a triaryl phosphine coordinated palladium complex, a system composed of triaryl phosphine ligand and a palladium salt or complex, and a use of the triaryl phosphine coordinated palladium complex in catalysing organic reactions, in particular a use in catalysis of coupling reactions involving (pseudo)halogenated aromatic hydrocarbon as substrate.

1 Claim, No Drawings

TRIARYL PHOSPHINE LIGANDS, PREPARATION METHOD THEREFOR, AND USE IN CATALYSING COUPLING REACTIONS

TECHNICAL FIELD

The invention relates to novel triaryl phosphine ligands (including P-chirality), preparation methods therefor, their use as key components in the catalytic system composed of post-transition metals, and their use in palladium-catalyzed organic reactions, especially in catalyzing coupling reactions, including C—C and C—X bond formation reactions.

BACKGROUND

A variety of organic reactions can be efficiently catalyzed by transition metal complexes. Therefore, transition metal catalysts often play an important role in the preparation of pharmaceuticals and organic materials. The performance of transition metal catalyst essentially depends on the metal element itself, but it can efficiently achieve a rich variety of organic transformations, including asymmetric transformations, as well as the contribution of the ligands around it to the regulation of the properties of metal center. Among them, organic ligands, especially phosphine ligands, play an important role in regulating the electronic properties of metal center and the stereoscopic environment around metal center. The σ-donating ability of the coordination atom and the π-accepting feedback electron ability regulate the electronic properties of the metal center and affect the coordination strength between the coordination atom in the para position and the metal center, the radius of the coordination atom and the peripheral size it occupies affect the coordination number of the metal center and the coordination arrangement of other ligands (including substrates). Therefore, the electronic and stereoscopic properties of the ligands synergistically and comprehensively affect the various steps of the catalytic reaction, and play a key role in catalyzing organic conversion of transition metals efficiently.

Among many organic reactions catalyzed by transition metals, coupling reaction is a very important type of reaction. Therefore, the development of highly efficient chiral or achiral phosphine ligands to achieve efficient catalytic coupling reactions has attracted much attention. The following FIGURE lists several electron-rich and large steric hindrance organic phosphine ligands with excellent performance for palladium-catalyzed coupling reaction. Fu et al. found that electron-rich, large steric hindrance of tri-tert-butyl phosphine has excellent performance in Pd-catalyzed coupling reactions, which has set off an upsurge in the development of such new phosphine ligands (A F Littke, et al., J. Am. Chem. Soc., 2000, 122, 4020). Beller of Germany and Hartwig of Yale University have respectively developed electron-rich, large sterically hindered diadamantyl phosphine (M. Beller, et al., CN 101195641) and polysubstituted phenyl ferrocene phosphine QPhos (J F Hartwig, et al. al., WO2002/011883), which have become commercial products. Takasago Corporation of Japan has developed a phosphine ligand with an aryl cyclopropyl skeleton (cBRIDP) (K. Suzuki, et al, WO2013/032035). Although Hiyashi et al. have already discovered that 1,1'-dibinaphthalene-2-phosphine and other biaryl phosphines have superior catalytic performance in palladium-catalyzed Kumada coupling reaction, Buchwald et al. expanded to biaryl phosphine and developed a series of excellent biaryl phosphines (S. L. Buchwald, et al., U.S. Pat. No. 6,307,087; WO 2009/076622). In addition to the characteristics of electron-rich and large steric hindrance, the π electrons in the benzene ring B in the biaryl phosphine can also produce weak coordination with the palladium center, which is an important reason for the excellent catalytic performance of biaryl phosphine ligands.

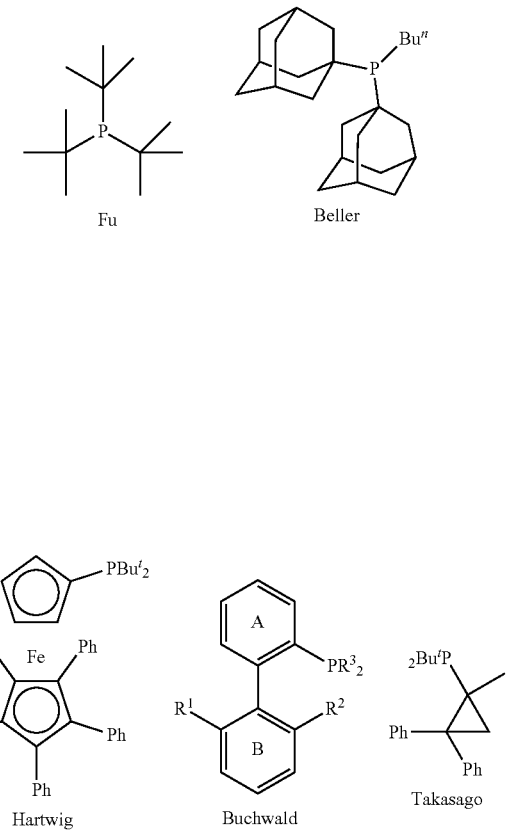

Although the Pd center faces the benzene ring B, and the coordination with the aryl electron is the dominant conformation with the lowest energy, as shown in the FIGURE below, there is a conformational twist that causes the Pd center to face the benzene ring B (T. E. Barder, et al., J. Am. Chem. Soc., 2007, 129, 5096). However, the catalytic activity of the pd-b-facing species is only equivalent to dicyclohexylphenylphosphine palladium, and even, it can form Pd—C bond to become dormant catalyst species. This is a defect of this kind of biaryl phosphine.

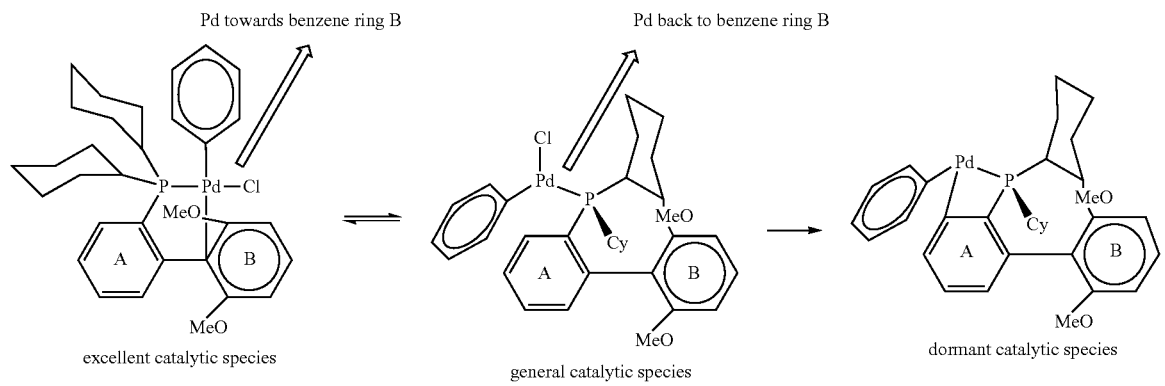

excellent catalytic species    general catalytic species    dormant catalytic species In order to overcome the defect caused by the lone pair of electrons on the phosphorus or the coordinated palladium center facing away from the benzene ring B. Buchwald et al. also prepared a biaryl phosphine with methyl or methoxy groups introduced on the benzene ring A, as shown in the FIGURE below, it is said that this conformation can facilitate the lone pair electrons or its coordination palladium center toward the benzene ring B. However, the introduction of methyl or methoxy groups still fails to completely compensate for this defect, due to the mutual repulsion between them and the substituents on the phosphorus atom or/and the coordination between oxygen atom and the palladium center. In the actual catalytic process, this conformation of palladium center back to benzene ring B can be as high as 33% (B. P. fors, D. A. Watson, M. R. Biscoe, S. L. Buchwald, J. Am. Chem. Soc., 2008, 130, 13552-13554). Of course, the introduced methyl or methoxy groups played a role in preventing Pd—C bond formation between palladium and benzene ring A and preventing the formation of dormant state. Haddad et al. used the oxymethylene chain to fix the conformation so that the lone pair electrons could only face benzene ring B, which completely solved the torsion defect of the conformation of biaryl phosphine(WO 2011/126917). This kind of biaryl phosphine ligands with conformation fixed by oxymethylene chain has superior catalytic performance, but there is a problem that the synthesis step is more than 10 steps.

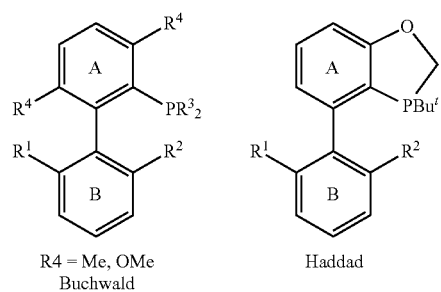

R4 = Me, OMe
Buchwald

Haddad

The results show that there is a benzene ring on both sides of the phosphorus atom in the triary phosphine ligands, so that the lone pair electrons on the phosphorus atom always have a benzene ring B that can be oriented, which can solve the defect of conformational torsion of biaryl phosphine by Buchwald et al. In order to obtain stable P=P double bond species, B. Twamley et al. prepared 2,6-bis(2,4,6-triisopropylphenyl)phenylphosphine dichloride (B. Twamley, et al., J. Am. Chem. Soc., 1999, 121, 3357-3367). For the purpose of developing optoelectronic materials, the large steric hindrance of triary phosphine is used to stabilize the P=P double bond species, K. Tsuji et al. prepared compounds with 2,6-bis(2,4,6-trimethylphenyl) phenylphosphorus skeleton (K. Tsuji, et al., Tetrahedron Lett., 1999, 40, 3203). In 2004, Smith et al. reported a triary phosphine, 2,6-bis (2,4,6-trimethylphenyl) phenyldimethylphosphine (DmpPMe2, R. C. Smith, et al., Tetrahedron Letters, 2004, 45, 8327-8330, see the FIGURE below), used in the palladium-catalyzed Suzuki coupling reaction, but due to the two methyl groups with less steric hindrance on the phosphorus atom, the catalytic performance of this triaryl phosphine obviously inferior to Buchwald's biaryl phosphine. Buster et al. also prepared triaryl phosphine (B. Buster, et al., Inorganica Chimica Acta, 2009, 362, 3465-3474), but the other two substitutions on the phosphorus atom are also methyl at the same time. Kondoh et al. prepared several triaryl phosphines, including 8b-S ligand, by studying the ring formation of triacetylenes catalyzed by rhodium, (A. Kondoh, et al., J. Am. Chem. Soc., 2007, 129, 6996-6997, see the FIGURE below), and it was found that 8b-S has higher catalytic activity in the Buchwald-Hartwig coupling reaction, however the preparation route of this phosphine ligand is long, the preparation of raw materials is not easy and the application of precious rhodium as a catalyst is involved. In addition, the two phenyl groups on the side of the phosphorus atom cannot avoid the defect of forming Pd—C bond dormant species. Recently, Sasaki et al. prepared bis(2,4,6-triisopropylphenyl)[4-bromo-2,6-bis(4-tert-butylphenyl)phenyl]phosphine (S. Sasaki, et al., Sulfur and Silicon, 2014, 189, 1207-1215), which is characterized in that the para position of the phosphorus atom is a bromine substituent, and it has not been used in the formation of a transition metal catalytic system. Rao et al. disclosed that 2,6-diphenyl-1-bromobenzene magnesium form a Grignard reagent, then react with biaryl phosphine chloride or di-tert-butylphosphine chloride under palladium catalysis to prepare (2,6-diphenyl)-phenyldiphenylphosphine ligand and (2,6-diphenyl)-phenyldi-tert-butylphosphine ligand (CN 105859774), however, no structural identification or physicochemical data of the compound is given. In fact, what Rao et al. wants to describe is the role of tetrakis (triaryl phosphine) palladium in the reaction of a sterically hindered Grignard reagent with a sterically hindered phosphine monochloride.

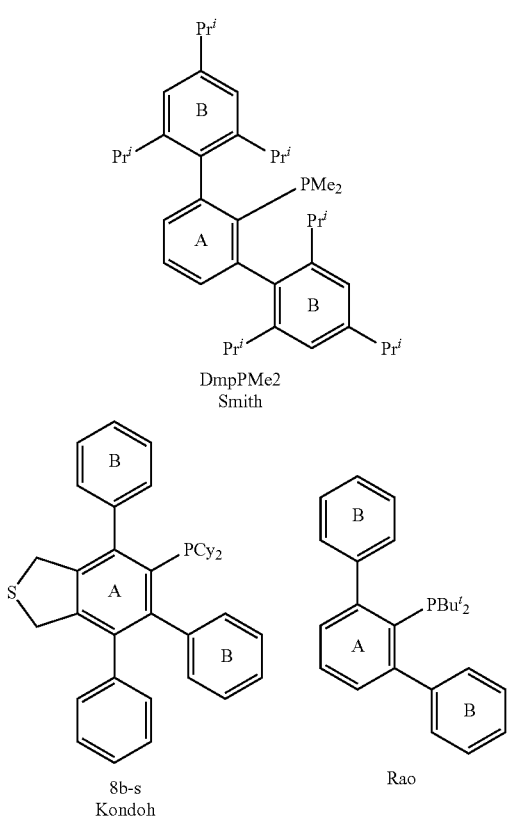

DmpPMe2
Smith 8b-s
Kondoh

Rao

In 2016, Ortega-Moreno et al. prepared a series of triaryl dialkyl (alkynyl) phosphines in "2 pots" (L. Ortega-Moreno, et al., Polyhedron, 2016, 116, 170-181. See the FIGURE below), but the other two substituents on the phosphorus atom are limited to groups with less steric hindrance: methyl, ethyl, propenyl, 3-butenyl or ethynyl.

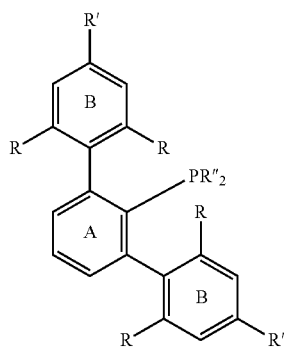

R=Me, R'=H: R"=Me, Et, CH2CH=CH2, CH2CH2CH=CH2; R=Pri, R'=H: R"=Me, Et, CH2CH=CH2; R=R'=Pri: R"=Me; R=R'=Me: R"=ethynyl.

According to the defect that the conformation of biaryl phosphine can be twisted by Buchwald et al., the invention specially designs and prepares triaryl phosphines. The inventiveness of the invention also includes the "one pot" preparation of a variety of new triaryl phosphines from cheap and easily available raw materials, such as m-dichlorobenzene, especially the introduction of substituents with large steric hindrance in phosphorus atom. In addition, triaryl phosphines, such as methoxy and isopropoxy, with heteroatom (oxygen, nitrogen) substituents on both sides of the aromatic ring, have not been reported. In the preparation of triaryl phosphine ligands with two tert butylphosphonates, the invention provides a two-step process, that is, the tert-phenyl anion is first reacted with the tert-butyl dichloride and then reacted with the tert-butyl anion, which is also the feature that the invention can prepare the tert-butyl sterically hindered substituent.

The catalytic performance of 2,6-bis(2,4,6-triisopropylphenyl)phenyl-dicyclohexylphosphine (XTPhos) in the palladium-catalyzed Suzuki-Miyaura coupling reaction is obviously better than DmpPMe2 developed by Smith et al. In addition, in the coupling reaction of carbazole and 4-chlorotoluene, the performance of XTPhos is better than cBRIDP phosphine ligand of Takasago company (which is better than XPhos phosphine ligand of Buchwald). The performance of 2,6-bis (2,4,6-triisopropylphenyl) phenyl dicyclohexylphosphine(ZTPhos) in palladium-catalyzed amination of chlorinated aromatic hydrocarbons is obviously better than that of 8b-S ligand developed by kondoh et al. Which also reflect the creativity of the invention.

SUMMARY

The invention relates to: (1) triaryl phosphine ligands; (2) preparation method of triaryl phosphine ligands; (3) palladium complexes coordinated by triaryl phosphines; (4) catalytic system formed by the combination of triaryl phosphine ligands and palladium salts or complexes; (5) catalytic system of the combination of triaryl phosphine ligands and palladium, including palladium complexes coordinated by triaryl phosphines, application in catalysis of coupling reactions involving halogenated aromatic hydrocarbon as substrate.

INVENTION DISCLOSURE

In the first aspect, triaryl phosphine ligands of general formula is Ia, Ib or their mixture,

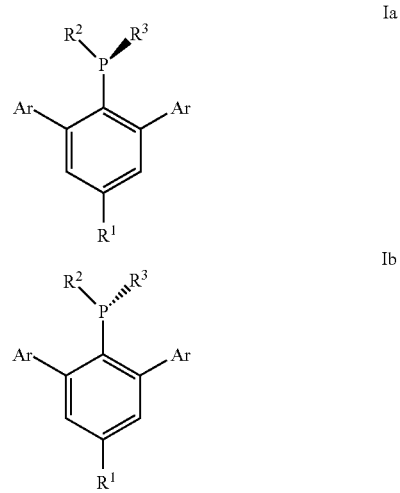

Wherein,
Ar is selected from (C6-C20) aryl, which may have 1 to 3 independently selected from (C1-C6) alkyl, —O(C1-C6) alkoxy, —N(C1-C6)$_2$ dialkylamino or (C6-C10) aryl substituents (the aryl group here can also have 1 to 3 independently selected from (C1-C6) alkyl, —O (C1-C6) alkoxy or —N(C1-C6)$_2$ substituent of dialkylamino), even Ar can be further selected from phenyl, 4-methylphenyl, 4-methoxyphenyl, 4-isopropylphenyl, 4-tert-butylphenyl, 4-(dimethylamino)phenyl, 4-fluorophenyl, 3,5-dimethylphenyl, 3,5-di-tert-butylphenyl, 2-methylphenyl, 2-methoxyphenyl, 2-(dimethylamino)phenyl, 2-isopropylphenyl, 2,6-dimethylphenyl, 2,6-diisopropylphenyl, 2,6-dimethoxyphenyl, 2,6-diisopropoxyphenyl, 2,6-bis(dimethylamino)phenyl, 2,6-dimethoxy-3,5-diphenyl-phenyl, 2,6-dimethoxy-3,5-bis(3,5-dimethylphenyl)-phenyl, 2,6-diisopropoxy-3,5-diphenyl-phenyl, 2,6-dimethoxy-3,5-bis(2,4,6-triisopropylphenyl)-phenyl, 2-methoxy-6-(dimethyl amino)phenyl, 2,4,6-trimethylphenyl, 2,4,6-trimethoxyphenyl, 2,4,6-triisopropylphenyl, ferrocene, 1-naphthyl, 2-naphthyl, 2-methoxy-1-naphthyl or 9-anthracenyl;

$R^1$ is selected from H, (C1-C6)alkyl, —O(C1-C6)alkoxy or —N(C1-C6)$_2$ dialkylamino; even further selected from one of H, methyl, methoxy, dimethylamino, isopropyl or tert-butyl;

$R^2$ and $R^3$ are each independently selected from (C1-C10) alkyl, (C3-C10) cycloalkyl, (5-11 membered) heterocycloalkyl, (C6-C20) aryl, (C4-C20) hetero aryl or —CH$_2$(C6-C10) arylmethylene, here (C3-C10) cycloalkyl, (5-11 membered) heterocycloalkyl, (C6-C20) aryl, (C4-C20) heteroaryl and —CH$_2$(C6-C10)arylene groups can have 1 to 3 independently selected from (C1-C6)alkyl or —O(C1-C6)alkoxy, —N(C1-C6)$_2$ substituents of dialkylamino groups, where the heteroatoms in the heteroaryl group are selected from O, N or S atom, even $R^2$ and $R^3$ can be further independently selected from methyl, ethyl, propyl, isopropyl, n-butyl, tert-butyl, cyclopentyl, cyclohexyl, adamantyl, phenyl, 2-methylphenyl, 2-isopropylphenyl, 2-methoxyphenyl, 2-(dimethylamino)phenyl, 4-methylphenyl, 4-fluorophenyl, 4-methoxyphenyl, 4-(dimethylamino)phenyl, 3,5-dimethylphenyl, 3,5-bis(trifluoromethyl)phenyl, 3,5-difluorophenyl, 3,5-di-tert-butylphenyl, 2,6-dimethylphenyl, 2,6-dimethoxyphenyl, 2,6-diisopropylphenyl, 2,4,6-trimethoxyphenyl, 2-biphenyl, 2',6'-dimethyl-2-biphenyl, 2',6'-dimethoxy-2-biphenyl, 2',6'-diisopropoxy-2-biphenyl, 2',6'-bisdimethylamino-2-biphenyl, 2',6'-diisopropyl-2-biphenyl, 2',4',6'-triisopropyl-2-biphenyl, ferrocene, 2-furanyl, 2-thienyl, 2-benzofuranyl, 2-benzothienyl, 2-pyridyl or 2-tetrahydrofuranyl;

When $R^1$=H and Ar=phenyl, $R^2$ and $R^3$ are not tert-butyl at the same time;

When $R^1$=H and $R^2$=$R^3$=methyl, Ar is not phenyl 3,5-dimethylphenyl, 2,6-dimethylphenyl, 2,6-diisopropylphenyl, 2,4,6-trimethylphenyl or 2,4,6-triisopropylphenyl;

When $R^1$=H and $R^2$=$R^3$=ethyl, Ar is not 2,6-dimethylphenyl, 2,4,6-trimethylphenyl or 2,6-diisopropylphenyl;

When $R^1$=H and $R^2$=$R^3$=2,4,6-trimethylphenyl, Ar is not 2-methylphenyl, 4-methylphenyl or 1-naphthyl.

In the second aspect, the preparation method of triaryl phosphine ligands (general formula Ia, Ib or their mixture). The preparation can be summarized as follows:

3,5-dichlorobenzene with substituent $R^1$ or 3,5-dichlorobenzene without substituent or 3-fluoro-5-chlorobenzene recats with butyllithium or sec-butyl at −100° C. to −70° C.;

Reacts with ArMgX (X can be Cl, Br or I) in the range of −100° C. to 140° C., the reaction temperature is increased in stages;

CuX$^1$ can be added or not (X$^1$ can be Cl, Br or I), or tetrakis (tiarylphosphine) palladium can be added or not, according to the type of phosphorus chloride reagent added, PCl$_3$, $R^2$PCl$_2$, $R^3$PCl$_2$ or $R^2R^3$PCl can be added in the range of −100° C. to 30° C.;

$R^2$M and/or $R^3$M(M=Li, Na, MgX$^1$, CuX$^1$, where X$^1$ can be Cl, Br or I)can be added according to the type of phosphorus chloride reagent added. One of the characteristics of the preparation method provided by the invention is that the preparation of triaryl phosphine ligands can be realized in "one pot" without separation and purification of intermediates.

In addition, 2,6-diarylphenyllithium or magnesium reagent can also be prepared by reaction of 2,6-diarylphenylbromide (iodine) (Mark C. Lipke, et al., organometallics, 2009, 28, 188-196) with normal (secondary or tertiary) butyl lithium, metal magnesium or isopropyl Grignard reagent, which is commonly known in the art; Reacts with PCl$_3$, $R^2$PCl$_2$, $R^3$PCl$_2$ or $R^2R^3$PCl, and then, CuX(X can be Cl, Br or I) can be added or not, or tetra (tiarylphosphine) palladium can be added or not;

Choose to add $R^2$M and/or $R^3$M (M=Li, Na, MgX$^1$ or CuX$^1$, where X$^1$ can be Cl, Br or I), according to the type of phosphorus chloride reagent added.

In the third aspect, the substituents selected from triaryl phosphine ligands can constitute the following specific phosphine compounds:

(2,6-Diphenyl-4-methylphenyl)-diphenylphosphine;
(2,6-Diphenyl-4-methylphenyl)-dicyclohexylphosphine;
(2,6-Diphenyl-4-methylphenyl)-di-tert-butylphosphine;
[2,6-Bis(2-methylphenyl)phenyl]-diphenylphosphine;
[2,6-Bis(2-methylphenyl)phenyl]-dicyclohexylphosphine;
[2,6-Bis(2-methylphenyl)phenyl]-di-tert-butylphosphine;
[2,6-Bis(2,6-dimethylphenyl)phenyl]-diphenylphosphine;
[2,6-Bis(2,6-dimethylphenyl)phenyl]-dicyclohexylphosphine;
[2,6-Bis(2,6-dimethylphenyl)phenyl]-cyclohexyl-2-thienylphosphine;
[2,6-Bis(2,6-dimethylphenyl)phenyl]-tert-butyl-2-furylphosphine;
[2,6-Bis(2,4,6-trimethylphenyl)phenyl]-[2-dimethylaminophenyl]-phenylphosphine;
[2,6-Bis(2,4,6-trimethylphenyl)phenyl]-[2-dimethylaminophenyl]-cyclohexylphosphine;
[2,6-Bis(2,4,6-trimethylphenyl)phenyl]-[2-dimethylaminophenyl]-tert-butylphosphine;
[2,6-Bis(2-methoxyphenyl)phenyl]-diphenylphosphine;
[2,6-Bis(2-methoxyphenyl)phenyl]-dicyclohexylphosphine;
[2,6-Bis(2-methoxyphenyl)phenyl]-di-tert-butylphosphine;
[2,6-Bis(2-methoxyphenyl)phenyl]-cyclohexyl-2-thienylphosphine;
[2,6-Bis(2-methoxyphenyl)phenyl]-methyl-tert-butylphosphine;
[2,6-Bis(2-methoxyphenyl)phenyl]-bis[3,5-bis(trifluoromethyl)phenyl]phosphine;
[2,6-Bis(2-methoxyphenyl)phenyl]-phenyl-[3,5-bis(trifluoromethyl)phenyl]phosphine;
[2,6-Bis(2,6-dimethoxyphenyl)phenyl]-diphenylphosphine;
[2,6-Bis(2,6-dimethoxyphenyl)phenyl]-dicyclohexylphosphine;
[2,6-Bis(2,6-dimethoxyphenyl)phenyl]-phenyl-isopropylphosphine;
[2,6-Bis(2,6-dimethoxyphenyl)phenyl]-cyclohexyl-2-thienylphosphine;
[2,6-Bis(2,6-dimethoxyphenyl)phenyl]-cyclohexyl-adamantylphosphine;
[2,6-Bis(2,6-dimethoxyphenyl)phenyl]-methyl-tert-butylphosphine;
[2,6-Bis(2,6-dimethoxyphenyl)phenyl]-bis[3,5-bis(trifluoromethyl)phenyl]phosphine;
[2,6-Bis(2,6-dimethoxyphenyl)phenyl]-phenyl-[3,5-bis(trifluoromethyl)phenyl]phosphine;

[2,6-Bis(2,6-diisopropoxyphenyl)phenyl]-diphenylphosphine;
[2,6-Bis(2,6-diisopropoxyphenyl)phenyl]-dicyclohexylphosphine;
[2,6-Bis(2,6-diisopropylphenyl)phenyl]-dicyclohexylphosphine;
[2,6-Bis(2,6-diisopropylphenyl)phenyl]-phenyl-cyclohexylphosphine;
[2,6-Bis(2,6-diisopropylphenyl)phenyl]-methyl-tert-butylphosphine;
[2,6-Bis(2,6-diisopropylphenyl)phenyl]-phenyl-isopropylphosphine;
[2,6-Bis(2,6-diisopropylphenyl)phenyl]-[2',6'-dimethyl-2-biphenyl]-methylphosphine;
[2,6-Bis(2,6-diisopropylphenyl)phenyl]-[2',6'-dimethoxy-2-biphenyl]-methylphosphine;
[2,6-Bis(2,6-diisopropylphenyl)phenyl]-[2',6'-dimethoxy-2-biphenyl]-cyclohexylphosphine;
[2,6-Bis(2,6-diisopropylphenyl)phenyl]-[2',6'-diisopropyl-2-biphenyl]-cyclohexylphosphine;
[2,6-Bis(2,6-diisopropylphenyl)phenyl]-bis[3,5-bis(trifluoromethyl)phenyl]phosphine;
[2,6-Bis(2,6-diisopropylphenyl)phenyl]-phenyl-[3,5-bis(trifluoromethyl)phenyl]phosphine;
[2,6-Bis(2,4,6-triisopropylphenyl)phenyl]-dicyclohexylphosphine;
[2,6-Bis(2,4,6-triisopropylphenyl)phenyl]-phenyl-cyclohexylphosphine;
[2,6-Bis(2,4,6-triisopropylphenyl)phenyl]-methyl-tert-butylphosphine;
[2,6-Bis(2,4,6-triisopropylphenyl)phenyl]-cyclohexyl-isopropylphosphine;
[2,6-Bis(2,4,6-triisopropylphenyl)phenyl]-[2',6'-dimethyl-2-biphenyl]-n-butylphosphine;
[2,6-Bis(2,4,6-triisopropylphenyl)phenyl]-[2',6'-dimethoxy-2-biphenyl]-methylphosphine;
[2,6-Bis(2,4,6-triisopropylphenyl)phenyl]-[2',6'-dimethoxy-2-biphenyl]-cyclohexylphosphine;
[2,6-Bis(2,4,6-triisopropylphenyl)phenyl]-[2',6'-diisopropyl-2-biphenyl]-tert-butylphosphine;
[2,6-Bis(2,4,6-triisopropylphenyl)phenyl]-bis[3,5-bis(trifluoromethyl)phenyl]phosphine;
[2,6-Bis(2,4,6-triisopropylphenyl)phenyl]-cyclohexyl-[3,5-bis(trifluoromethyl)phenyl]phosphine;
[2,6-Bis(2-methoxy-1-naphthyl)phenyl]-diphenylphosphine;
[2,6-Bis(2-methoxy-1-naphthyl)phenyl]-dicyclohexylphosphine;
[2,6-Bis(2-methoxy-1-naphthyl)phenyl]-di-tert-butylphosphine;
[2,6-Bis(2-methoxy-1-naphthyl)phenyl]-(2-dimethylaminophenyl)-cyclohexylphosphine;
[2,6-Bis(2-methoxy-1-naphthyl)phenyl]-(4-dimethylaminophenyl)-cyclohexylphosphine;
[2,6-Bis(2-methoxy-1-naphthyl)phenyl]-[2',6'-dimethoxy-2-biphenyl]-n-butylphosphine;
[2,6-Bis(2-methoxy-1-naphthyl)phenyl]-[2',6'-diisopropyl-2-biphenyl]-cyclohexylphosphine;
[2,6-Bis(2-methoxy-1-naphthyl)phenyl]-bis[3,5-bis(trifluoromethyl)phenyl]phosphine;
[2,6-Bis(2-methoxy-1-naphthyl)phenyl]-[3,5-bis(trifluoromethyl)phenyl]-methylphosphine;
[2,6-Bis(2-isopropoxy-1-naphthyl)phenyl]-diphenylphosphine;
[2,6-Bis(2-isopropoxy-1-naphthyl)phenyl]-dicyclohexylphosphine;
[2,6-Bis(2-methoxy-6-dimethylaminophenyl)phenyl]-diphenylphosphine;
[2,6-Bis(2-methoxy-6-dimethylaminophenyl)phenyl]-dicyclohexylphosphine;
[2,6-Bis(2,6-dimethylaminophenyl)phenyl]-diphenylphosphine;
[2,6-Bis(2,6-dimethylaminophenyl)phenyl]-dicyclohexylphosphine.

In the fourth aspect, triaryl phosphines are used as supporting ligands in combination with transition metal complexes or transition metal salts of elements of group VIII or IB of the periodic table, such as palladium, nickel, platinum, rhodium, iridium, ruthenium, cobalt or gold, and used as catalysts. Generally, the triaryl phosphines can be added to suitable transition metal precursors to generate a catalytic system in situ.

In the fifth aspect, a series of palladium complexes with triaryl phosphines have the general formula II, III, IV, V, VI or VII

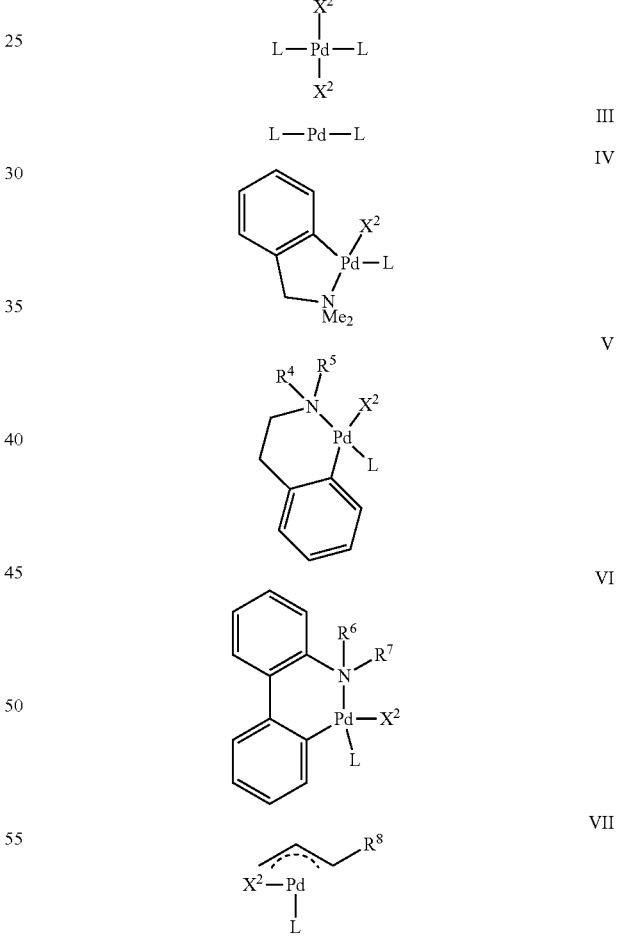

Wherein,
L is triaryl phosphine ligand defined above;
$X^2$ is Cl, Br, I, methanesulfonic acid, benzenesulfonic acid, p-toluenesulfonic acid, formic acid, acetic acid, or benzoic acid;
$R^4$, $R^5$, $R^6$, $R^7$ or $R^8$ is each independently selected from H, methyl or phenyl.

The invention further provides the application of in-situ produced palladium catalytic system and palladium complex in catalyzing Suzuki coupling and Buchwald-Hartwig amination reaction. Meanwhile, the catalytic system can also be used for other transition metal catalyzed reactions which are obvious to those skilled in the art, especially Negishi coupling, Kumada coupling, Sonogashira alkynylation and Heck coupling.

Generally speaking, it is more advantageous to use palladium complex as catalyst precursor for catalytic reaction, and in some cases, the induction period of catalytic system will be shortened. Even if palladium complex is directly used as the catalyst precursor, sometimes additional relative to palladium, 0.5 to 100 times of the triaryl phosphine ligands provided by the invention are added, which generally increases the service life of the catalytic system.

There are many palladium sources which can form a catalyst in situ with phosphine ligands of the invention, including palladium acetate, palladium chloride, palladium acetylacetonate, palladium diphenylmethylene acetone, tetrakis(tiarylphosphine) palladium, diacetonitrile palladium chloride, 2-aminobiphenyl-2-palladium chloride, or other palladium sources are well known to those skilled in the art.

The phosphine ligands of the invention has good thermal stability in inert atmosphere, so the catalyst system provided by the invention can be used at the temperature up to 200° C. or higher. It is advantageous to carry out catalytic reaction at the reaction temperature of 20° C. to 180° C. or even 40° C. to 130° C. Triaryl phosphine ligands can also be used in the pressurization reaction, and usually the pressure can reach 100 atmospheres, however, the reaction is preferably carried out from atmospheric pressure not higher than the range of 60 atmospheres to normal atmospheric pressure.

EXEMPLIFICATION

The following examples illustrate specific embodiments of the invention, but don't mean that the invention is limited to the following examples.

Definitions

The term "THF" is art-recognized and refers to tetrahydrofuran.

The term "TMEDA" is art-recognized and refers to N,N,N',N'-tetramethylethylenediamine.

Preparation method of Grignard reagent. To an oven-dried 100 mL three-necked flask, equipped with a stir bar, a condenser tube, a constant pressure funnel and a suction connector, and add magnesium in an inert atmosphere. The mixture of THF and bromine aromatic hydrocarbon are placed in a constant pressure funnel, and about 1 mL is first added into the three-necked flask. After the reaction is initiated, the remaining mixture is dropped into the three-necked flask (about 15 min) while maintaining a slight boiling. React in an oil bath at 70° C. for 2 to 5 h, then cool to room temperature for later use.

Example 1.
(2,6-Diphenyl-4-methylphenyl)-diphenylphosphine

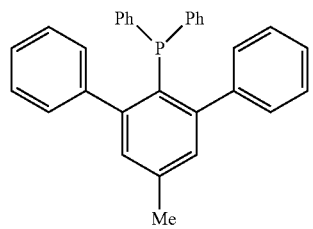

Example 1-1

To an oven-dried 250 mL flask, equipped with a magnetic stir bar and a condenser, was charged with magnesium (0.29 g, 12.0 mmol), THF (10 mL) and bromobenzene (1.73 g, 11.0 mmol) heated to reflux for 2 h to obtain a Grignard reagent.

To another oven-dried two-neck 250 mL flask was added THF (15 mL) and 3,5-dichlorotoluene (0.81 g, 5.0 mmol), n-butyllithium (2.4 mL of a 2.5 M solution in hexanes, 6.0 mmol) was added dropwise at −78° C. and stirred for 30 min. At that point the Grignard reagent was transferred via cannula to the solution, then warmed to room temperature, and the reaction solution was heated to 80° C. for 6 h. Cooled to −78° C. again, then $Ph_2PCl$ (1.32 g, 6.0 mmol) was added dropwise via cannula and the solution was warmed to room temperature for 6 h. The solvent was a removed in vacuum and 50 mL of brine was added, and the mixture was extract with dichloromethane three times (3×40 mL), and the combined organic phase was washed with brine, dried over anhydrous sodium sulfate and concentrated in vacuum. The residue was purified by column chromatography to give 1.39 g of 2,6-bisphenyl-4-methylphenyl-diphenylphosphine as a white crystalline material, 65% yield. m.p.: 144.3-145.9° C.

$^1$H NMR (400 MHz, $CDCl_3$) δ: 7.14 (d, J=2.7 Hz, 3H), 7.13 (s, 1H), 7.12-7.07 (m, 10H), 7.06 (t, J=4.3 Hz, 8H), 2.46 (s, 3H).
$^{13}$C NMR (101 MHz, $CDCl_3$) δ: 150.29, 150.13, 143.10, 143.05, 138.80, 137.65, 137.53, 132.45, 132.26, 131.70, 131.66, 129.24, 129.22, 127.65, 127.59, 127.31, 127.00, 126.46, 21.12.
$^{31}$P NMR (162 MHz, $CDCl_3$) δ: −6.85.
HR-MS m/z (%): Calcd for $C_{31}H_{25}P$ [M] 428.1688; Found 428.1671 (100).

Example 1-2

To an oven-dried 100 mL flask, equipped with a magnetic stir bar and a condenser, was charged with 2,6-diphenyl-4-methyliodobenzene (0.74 g, 2.0 mmol) and THF (3.0 mL) under nitrogen atmosphere. Cooled to −78° C., 0.89 mL n-butyllithium (2.7 M solution in hexanes, 2.4 mmol) was added dropwise in about 8 min, and the solution was reacted for 2 h. Then $Ph_2PCl$ (0.44 g, 2.0 mmol) was added dropwise via cannula and the solution was warmed to room temperature for 6 h. The solvent was a removed in vacuum and 20 mL of brine was added, then the mixture was extracted with dichloromethane (3×20 mL), and the combined organic phase was washed with brine, dried over anhydrous sodium sulfate and concentrated in vacuum to give a light yellow oil.

The residue was purified by column chromatography to give 0.60 g of (2,6-disphenyl-4-methylphenyl)-diphenylphosphine as a white crystalline material (71% of yield).

Example 1-3

To an oven-dried 50 mL flask, equipped with a magnetic stir bar and a condenser, was charged with magnesium (0.06 g, 2.2 mmol), and THF (5 mL), and 2,6-diphenyl-4-methyliodobenzene (0.74 g, 2.0 mmol) was added and the mixture was heated to reflux for 2 h to obtain a Grignard reagent. Then Ph₂PCl (1.32 g, 6.0 mmol) was added dropwise via cannula at −78° C. and the solution was warmed to room temperature for 6 h. The solvent was a removed in vacuum and 20 mL of brine was added, then the mixture was extracted with dichloromethane three times (3×20 mL), and the combined organic phase was washed with brine, dried over anhydrous sodium sulfate and concentrated in vacuum to give a light yellow oil. The residue was purified by column chromatography to give 0.60 g of (2,6-disphenyl-4-methylphenyl)-diphenylphosphine as a white crystalline material, 69% yield.

Example 2.
2,6-Diphenyl-4-methylphenyl-dicyclohexylphosphine

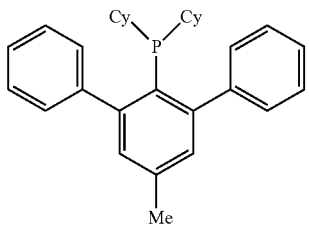

To an oven-dried 100 mL flask, equipped with a magnetic stir bar and a condenser, was charged with 2,6-diphenyl-4-methyliodobenzene (1.85 g, 5.0 mmol) and THF (10.0 mL). Cooled to −78° C., 2.04 mL n-butyllithium (2.5 M solution in hexanes, 5.5 mmol) was added dropwise about 8 min, and the reaction solution was reacted for 2 h at −78° C. Then the solution of Cy₂PCl (1.16 g, 5.0 mmol) in THF (3.0 mL) was added dropwise with cannula and the resulted reaction mixture was warmed to room temperature and stirred for 6 h. The solvent was a removed in vacuum and 20 mL of brine was added, then the mixture was extracted with dichloromethane (3×20 mL), and the combined organic phase was washed with brine, dried over anhydrous sodium sulfate and concentrated in vacuum to give a light yellow oil. The residue was purified by column chromatography to give 1.21 g of 2,6-diphenyl-4-methylphenyl-dicyclohexylphosphine as a white crystalline material, 55% yield. m.p.: 138.3-139.6° C.

¹H NMR (500 MHz, CDCl₃) δ: 7.41 (s, 6H), 7.31 (s, 4H), 7.06-7.02 (m, 2H), 2.39 (s, 3H), 1.31 (s, 22H).

¹³C NMR (126 MHz, CDCl₃) δ: 144.44, 144.40, 137.22, 131.20, 131.18, 129.89, 129.87, 127.22, 126.61, 35.80, 35.69, 32.91, 32.71, 31.96, 31.53, 31.45, 29.72, 29.68, 29.39, 27.06, 26.99, 26.97, 26.86, 26.26, 22.71, 20.90, 14.13.

³¹P NMR (202 MHz, CDCl₃) δ: −0.53.

HR-MS m/z (%): Calcd for C₃₁H₃₈P [M⁺+H] 441.2705; Found 441.2734 (100).

Example 3.
2,6-Bis(2-methylphenyl)phenyl-diphenylphosphine

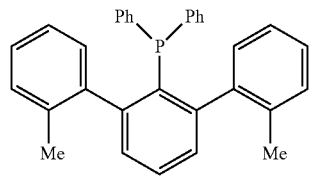 [SMILES: Cc1ccccc1-c1cccc(-c2ccccc2C)c1P(c1ccccc1)c1ccccc1]

To an oven-dried 100 mL flask, equipped with a magnetic stir bar and a condenser, was charged with 2,6-bis(2-methylphenyl)iodobenzene ((1.54 g, 4.0 mmol) and THF (4.0 mL). Cooled to −78° C. 6.8 mL t-butyllithium (1.3 M solution in hexanes, 8.8 mmol) was added dropwise about 8 min, and the reaction solution was reacted for 2 h. To another oven-dried 100 mL flask, equipped with a magnetic stir bar and a condenser, was charged with CuCl (0.48 g, 4.8 mmol), the lithium reagent was transferred via cannula to the flask was stirred for 20 min. Then Ph₂PCl (0.88 g, 4.0 mmol) was added dropwise via cannula at −78° C. and the solution was warmed to room temperature for 6 h. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 0.91 g of 2,6-bis(2-methylphenyl)phenyl-diphenylphosphine as a white crystalline material (52% yield). m.p.: 146.5-147.3° C.

¹H NMR (400 MHz, CDCl₃) δ: 7.49 (dd, J=14.6, 7.0 Hz, 1H), 7.22-6.70 (m, 20H), 1.92 (d, J=30.1 Hz, 6H).

¹³C NMR (101 MHz, CDCl₃) δ: 149.02, 148.85, 142.06, 135.30, 132.86, 132.66, 130.33, 130.29, 129.48, 129.24, 129.22, 129.10, 127.42, 127.35, 127.22, 127.06, 124.55, 20.82, 1.05.

³¹P NMR (162 MHz, CDCl₃) δ: −5.37, −7.65.

HR-MS m/z (%): Calcd for C₃₂H₂₈P [M⁺+H] 443.1923; Found 443.1903 (100).

Example 4. 2,6-Bis(2,6-dimethylphenyl)phenyl-diphenylphosphine

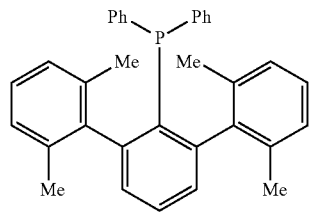 [SMILES: Cc1cccc(C)c1-c1cccc(-c2c(C)cccc2C)c1P(c1ccccc1)c1ccccc1]

Example 4-1

To an oven-dried 100 mL flask, equipped with a magnetic stir bar and a condenser, and charged with magnesium (0.61 g, 25.0 mmol), ca. 1 mL of a solution of 2,6-dimethylbromobenzene (4.44 g, 24.0 mmol) in THF (10.0 mL) was added and heated. After the reaction was initiated, the rest 2,6-dimethylbromobenzene solution was added dropwise and the reaction mixture was heated to reflux for 2 h to obtain the Grignard reagent.

To another oven-dried two-neck 250 mL flask was added THF (15 mL) and 1,3-dichlorobenzene (1.47 g, 10.0 mmol), n-butyllithium (4.8 mL of a 2.5 M solution in hexanes, 12.0 mmol) was added dropwise at −78° C. and stirred for 2 h. At that point the Grignard reagent was transferred via cannula to the solution, then warmed to room temperature, and the reaction solution was heated to 80° C. for 6 h. To the third oven-dried 250 mL flask, equipped with a magnetic stir bar and a condenser, was charged with CuCl (1.20 g, 12.0 mmol), the above prepared reaction mixture was transferred via cannula and the mixture was a stirred for 20 min. Then Ph$_2$PCl (2.64 g, 12 mmol) was added dropwise via cannula and the solution was heated to 80° C. for 6 h. Cooled to room temperature, 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 2.91 g of 2,6-bis(2,6-dimethylphenyl)phenyl-diphenylphosphine as a white crystalline material, 62% yield. m.p.: 149.5-150.9° C.

$^1$H NMR (400 MHz, CDCl$_3$) δ: 7.51 (t, J=7.6 Hz, 1H), 7.16-7.06 (m, 8H), 7.05-6.99 (m, 4H), 6.99-6.92 (m, 2H), 6.82 (d, J=7.6 Hz, 4H), 2.05 (s, 12H).

$^{13}$C NMR (101 MHz, CDCl$_3$) δ: 147.15, 147.00, 141.32, 141.28, 136.72, 136.60, 136.00, 135.99, 134.71, 134.48, 130.39, 130.36, 129.16, 127.92, 127.32, 127.23, 127.18, 21.55, 21.52.

$^{31}$P NMR (162 MHz, CDCl$_3$) δ: −2.18.

HR-MS m/z (%): Calcd for C$_{34}$H$_{32}$P [M$^+$+H] 471.2251; Found 471.2239 (100).

Example 4-2

To an oven-dried 100 mL flask, equipped with a magnetic stir bar and a condenser, was charged with 2,6-bis(2,6-dimethylphenyl)iodobenzene (1.24 g, 3.0 mmol) and THF (5.0 mL). Cooled to −78° C. 5.1 mL t-butyllithium (1.3 M solution in hexanes, 6.6 mmol) was added dropwise about 8 min, and the reaction solution was reacted for 2 h. To another oven-dried 100 mL flask, equipped with a magnetic stir bar and a condenser, was charged with CuCl (0.48 g, 4.8 mmol), the reaction mixture was transferred via cannula to the flask was stirred for 20 min. Then Ph$_2$PCl (0.99 g, 4.5 mmol) was added dropwise via cannula at −78° C. and the solution was warmed to room temperature for 6 h. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 0.90 g of 2,6-bis(2,6-dimethylphenyl)phenyl-diphenylphosphine as a white crystalline material (64% yield).

Example 5. [2,6-Bis(2,6-dimethylphenyl)phenyl]-2-thienylcyclohexylphosphine

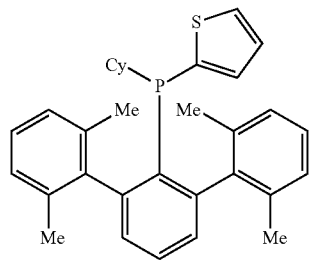

To an oven-dried 100 mL flask, equipped with a magnetic stir bar and a condenser, and charged with magnesium (0.61 g, 25.0 mmol), ca. 1 mL of a solution of 2,6-dimethylbromobenzene (4.44 g, 24.0 mmol) in THF (10.0 mL) was added and heated. After the reaction was initiated, the rest 2,6-dimethylbromobenzene solution was added dropwise and the reaction mixture was heated to reflux for 2 h to obtain a Grignard reagent.

To another oven-dried two-neck 250 mL flask was added THF (15 mL) and 1,3-dichlorobenzene (1.47 g, 10.0 mmol), n-butyllithium (4.8 mL of a 2.5 M solution in hexanes, 12.0 mmol) was added dropwise at −78° C. and stirred for 2 h. At that point the Grignard reagent prepared was transferred via cannula to the solution, then warmed to room temperature, and the reaction solution was heated to 80° C. for 6 h, and cooled to room temperature. To a third oven-dried 250 mL flask, equipped with a magnetic stir bar and a condenser, and charged with CuCl (1.19 g, 12.0 mmol), the above reaction solution was transferred via cannula and the mixture was a stirred for 20 min, then a mixture of CyPCl$_2$ (2.22 g, 12.0 mmol) and THF (10.0 mL) was added dropwise via cannula and the solution was heated to 40° C. for 6 h. The magnesium 2-thienyl bromide (36.0 mmol) was added in −80° C. and the solution was heated to 70° C. for 12 h. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 2.45 g of [2,6-bis(2,6-dimethylphenyl)phenyl-2-thienylcyclohexylphosphine as an orange crystalline material (48% yield). m.p.: 149.9-151.6° C.

$^1$H NMR (400 MHz, CDCl$_3$) δ: 7.60-7.52 (m, 1H), 7.49-7.44 (m, 1H), 7.40-7.32 (m, 2H), 7.31-7.25 (m, 2H), 7.12-6.99 (m, 4H), 6.85-6.78 (m, 1H), 6.02-5.94 (m, 1H), 2.42-2.27 (m, 1H), 2.20 (s, 6H), 1.81-1.74 (m, 1H), 1.69 (s, 6H), 1.66-1.58 (m, 3H), 1.56-1.46 (m, 2H), 1.38-1.29 (m, 1H), 1.27-1.18 (m, 1H), 1.15-1.00 (m, 2H).

$^{13}$C NMR (101 MHz, CDCl$_3$) δ: 148.63, 148.49, 139.81, 139.74, 137.22, 136.47, 136.43, 134.82, 132.62, 132.55, 131.87, 131.85, 131.18, 131.11, 128.99, 128.58, 128.49, 128.19, 128.11, 127.54, 127.17, 126.90, 126.56, 34.87, 34.58, 31.67, 31.57, 30.21, 30.13, 26.39, 26.23, 26.19, 26.03, 25.45, 21.50, 20.76.

$^{31}$P NMR (162 MHz, CDCl$_3$) δ: −13.70.

Example 6. [2,6-Bis(2,4,6-trimethylphenyl)phenyl]-[2-dimethylaminophenyl]-phenylphosphine

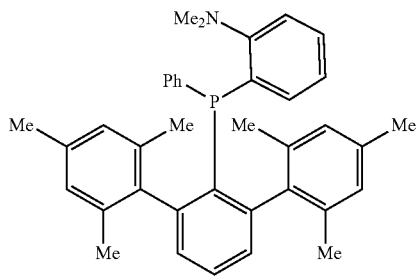 [SMILES: Cc1cc(C)c(-c2cccc(-c3c(C)cc(C)cc3C)c2P(c2ccccc2)c2ccccc2N(C)C)c(C)c1]

To an oven-dried 100 mL flask, equipped with a magnetic stir bar and a condenser, and charged with magnesium (0.61 g, 25.0 mmol), ca. 1 mL of a solution of 2,4,6-trimethylbromobenzene (4.78 g, 24.0 mmol) in THF (10.0 mL) was added and heated. After the reaction was initiated, the rest 2,4,6-trimethylbromobenzene solution was added dropwise and the reaction mixture was heated to reflux for 2 h to obtain a Grignard reagent.

To another oven-dried two-neck 250 mL flask with THF (15 mL) and 1,3-dichlorobenzene (1.47 g, 10.0 mmol), n-butyllithium (4.8 mL of a 2.5 M solution in hexanes, 12.0 mmol) was added dropwise at −78° C. and stirred for 2 h. At that point the Grignard reagent was transferred via cannula to the solution, then warmed to room temperature, and the reaction solution was heated to 80° C. for 6 h and then cooled to room temperature. To a third oven-dried 250 mL flask, equipped with a magnetic stir bar and a condenser, was charged with CuCl (1.20 g, 12.0 mmol), the above reaction solution was transferred via cannula and the mixture was a stirred for 20 min. A mixture of PhPCl$_2$ (2.15 g, 12.0 mmol) and THF (10.0 mL) was added dropwise via cannula and the solution was heated to 40° C. for 6 h. The magnesium 2-dimethylaminophenyl bromide (30.0 mmol) was added in −80° C. and the solution was heated to 70° C. for 12 h. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 3.08 g of [2,6-bis(2,4,6-trimethylphenyl)phenyl]-[2-dimethylaminophenyl]-phenylphosphine as an orange crystalline material (57% yield). m.p.: 151.2-152.9° C.

$^1$H NMR (400 MHz, CDCl$_3$) δ: 7.62-7.47 (m, 2H), 7.46-7.30 (m, 2H), 7.26-7.17 (m, 2H), 7.09-6.96 (m, 4H), 6.94-6.86 (m, 2H), 6.85-6.75 (m, 2H), 6.39-6.24 (m, 2H), 2.39 (s, 9H), 2.16 (s, 9H), 1.51 (s, 6H).

$^{31}$P NMR (162 MHz, CDCl$_3$) δ: −19.14.

HR-MS m/z (%): Calcd for C$_{38}$H$_{41}$NP [M$^+$+H] 542.2971; Found 542.2975(100).

Example 7. [2,6-bis(2-methoxyphenyl)phenyl]-diphenylphosphine

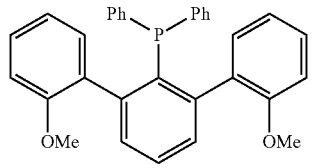 [SMILES: COc1ccccc1-c1cccc(-c2ccccc2OC)c1P(c1ccccc1)c1ccccc1]

To an oven-dried 100 mL flask, equipped with a magnetic stir bar and a condenser, was charged with 2,6-bis(2-methoxylphenyl)-iodobenzene (0.83 g, 2.0 mmol) and TH (5.0 mL). Cooled to −78° C., 3.4 mL t-butyllithium (1.3 M solution in hexanes, 4.4 mmol) was added dropwise about 8 min, and the reaction solution was reacted for 2 h. Then Ph$_2$PCl (0.44 g, 2.0 mmol) was added dropwise via cannula at −78° C. and the solution was warmed to room temperature for 6 h. The solvent was a removed in vacuum and 20 mL of brine was added, then the mixture was extracted with dichloromethane (3×20 mL), and the combined organic phase was washed with brine, dried over anhydrous sodium sulfate and concentrated in vacuum to give a light yellow oil. The residue was purified by column chromatography to give 0.76 g of [2,6-bis(2-methoxyphenyl)phenyl]-diphenylphosphine as a white crystalline material, 80% yield. m.p.: 144.6-146.1° C.

$^1$H NMR (500 MHz, CDCl$_3$) δ: 7.50-7.44 (m, 1H), 7.25-7.17 (m, 3H), 7.15-7.13 (m, 1H), 7.11-6.96 (m, 12H), 6.91-6.85 (m, 2H), 6.74-6.63 (m, 2H), 6.52-6.46 (m, 2H), 3.59 (s, 3H), 3.38 (s, 3H).

$^{13}$C NMR (126 MHz, CDCl$_3$) δ: 156.48, 155.81, 145.99, 145.86, 145.72, 145.60, 133.09, 132.98, 132.92, 132.83, 132.59, 132.43, 131.72, 131.68, 131.65, 131.25, 131.24, 131.08, 131.05, 130.98, 130.95, 130.87, 130.85, 128.46, 128.30, 127.25, 127.20, 127.17, 127.12, 126.94, 126.88, 126.78, 126.65, 126.58, 119.37, 109.89, 109.71, 54.65, 54.46.

$^{31}$P NMR (162 MHz, CDCl$_3$) δ: −3.40, −5.52.

HR-MS m/z (%): Calcd for C$_{32}$H$_{28}$O$_2$P [M$^+$+H] 475.1821; Found 475.1856(100).

Example 8. [2,6-bis(2-methoxyphenyl)phenyl]-dicyclohexylphosphine(HTPhos)

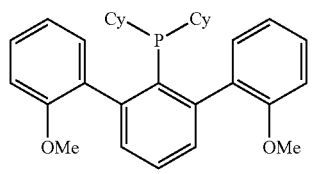

To an oven-dried 100 mL flask, equipped with a magnetic stir bar and a condenser, was charged with 2,6-bis(2-methoxylphenyl)-iodobenzene (0.83 g, 2.0 mmol) and TH (5.0 mL). Cooled to −78° C., 3.4 mL t-butyllithium (1.3 M solution in hexanes, 4.4 mmol) was added dropwise about 8 min, and the reaction solution was reacted for 2 h. Then Cy$_2$PCl (0.47 g, 2.0 mmol) was added dropwise via cannula at −78° C. and the solution was warmed to room temperature for 6 h. The solvent was a removed in vacuum and 20 mL of brine was added, then the mixture was extracted with dichloromethane (3×20 mL), and the combined organic phase was washed with brine, dried over anhydrous sodium sulfate and concentrated in vacuum to give a light yellow oil. The residue was purified by column chromatography to give 0.76 g of [2,6-bis(2-methoxyphenyl)phenyl]-dicyclohexylphosphine as a white crystalline material, 78% yield. m.p.: 143.2-145.1° C.

$^1$H NMR (500 MHz, CDCl$_3$) δ: 7.37-7.31 (m, 3H), 7.17-7.06 (m, 4H), 7.00-6.95 (m, 2H), 6.94-6.90 (m, 2H), 3.75 (s, 6H), 1.63-1.58 (m, 2H), 1.55-1.46 (m, 6H), 1.46-1.35 (m, 3H), 1.12-1.00 (m, 5H), 0.97-0.91 (m, 3H), 0.87-0.79 (m, 3H).

$^{31}$P NMR (202 MHz, CDCl$_3$) δ: 5.75, 5.24.

HR-MS m/z (%): Calcd for C$_{32}$H$_{40}$O$_2$P [M$^+$+H] 487.2760; Found 487.2762(100).

Example 9. [2,6-bis(2-methoxyphenyl)phenyl]-di-tert-butylphosphine

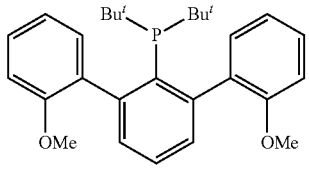

To an oven-dried 100 mL flask, equipped with a magnetic stir bar and a condenser, was charged with 2,6-bis(2-methoxylphenyl)-iodobenzene (0.83 g, 2.0 mmol) and THE (5.0 mL). Cooled to −78° C., 3.4 mL t-butyllithium (1.3 M solution in hexanes, 4.4 mmol) was added dropwise about 15 min, and the reaction solution was reacted for 1 h. Then added the mixture of $^t$BuPCl$_2$(0.32 g, 2.0 mmol) and THE (3.0 mL) was added and stirred for 1 h, after that warmed to room tempeture for 6 h. Then t-BuLi (2.2 mL of a 1.0 M in pentane, 2.9 mmol) and mixture of CuCl (0.25 g, 2.5 mmol) and THE (10.0 mL) was added dropwise and the reaction solution was stirred for 1 h, then the reaction solution was heated to reflux for 24 h. Cooled to room tempeture, 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 0.27 g of [2,6-bis(2-methoxyphenyl)phenyl]-di-tert-butylphosphine as a white crystalline material), 31% yield.

$^{31}$P NMR (162 MHz, CDCl$_3$) δ: 23.69.

Example 10. [2,6-Bis(2,6-dimethoxyphenyl)phenyl]-diphenylphosphine

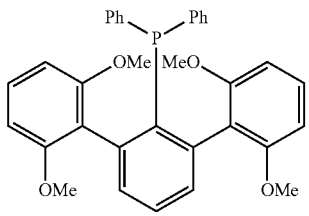 [SMILES: COc1cccc(OC)c1-c1cccc(-c2c(OC)cccc2OC)c1P(c1ccccc1)c1ccccc1]

Example 10-1

To an oven-dried 100 mL flask, equipped with a magnetic stir bar and a condenser, and charged with magnesium (0.29 g, 12.0 mmol), ca. 1 mL of a solution of 2,6-dimethoxybromobenzene (2.39 g, 11.0 mmol) in THE (10.0 mL) was added and heated. After the reaction was initiated, the rest solution was added dropwise and the reaction mixture was heated to reflux for 2 h to obtain a Grignard reagent. To another oven-dried two-neck 250 mL flask charged with TH (15 mL) and 3-chlorofluorobenzene (1.47 g, 5.0 mmol), n-butyllithium (2.4 mL of a 2.5 M solution in hexanes, 6.0 mmol) was added dropwise at −78° C. and stirred for 2 h. At that point the Grignard reagent was transferred via cannula to the solution, then warmed to room temperature, and the reaction solution was heated to 80° C. for 6 h. To a third oven-dried 250 mL flask, equipped with a magnetic stir bar and a condenser, and charged with CuCl (0.6 g, 6.0 mmol), the above reaction solution was transferred via cannula and the mixture was a stirred for 20 min. Ph$_2$PCl(1.32 g, 6.0 mmol) was added dropwise via cannula and the solution was heated to 70° C. for 3 h. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 1.15 g of [2,6-bis(2,6-dimethoxyphenyl)phenyl]-diphenylphosphine as a orange crystalline material, 43% yield. m.p.: 154.2-156.2° C.

$^1$H NMR (400 MHz, CDCl$_3$) δ: 7.52 (dd, J=10.6, 4.5 Hz, 1H), 7.16-6.85 (m, 14H), 6.29-6.13 (m, 4H), 3.53 (d, J=1.5 Hz, 12H).

$^{13}$C NMR (101 MHz, CDCl$_3$) δ: 157.42, 141.41, 141.24, 137.46, 137.33, 135.37, 135.17, 133.96, 133.75, 131.34, 128.79, 128.57, 126.77, 126.70, 119.92, 119.86, 103.08, 55.12.

$^{31}$P NMR (162 MHz, CDCl$_3$) δ: −2.99.

HR-MS m/z (%): Calcd for C$_{34}$H$_{32}$O$_4$P [M$^+$+H] 535.2032; Found 535.2029 (100).

Example 10-2

To an oven-dried 100 mL flask, equipped with a magnetic stir bar and a condenser, and charged with magnesium (0.67 g, 27.5 mmol), ca. 1 mL of a solution of 2,6-dimethoxybromobenzene (5.4 g, 25.0 mmol) in THE (15.0 mL) was added and heated. After the reaction was initiated, the rest solution was added dropwise and the reaction mixture was heated to reflux for 2 h to obtain a Grignard reagent. To another oven-dried two-neck 250 mL flask with THE (15 mL) and 1,3-dichlorobenzene (1.47 g, 10.0 mmol), 5.0 mL n-butyllithium (2.5 M solution in hexanes, 12.0 mmol) was added dropwise at −78° C. and stirred for 1 h. At that point the Grignard reagent was transferred via cannula to the solution, then warmed to room temperature, and the reaction solution was heated to 70° C. for 6 h. Then added the mixture of Pd(PPh$_3$)$_4$ (0.17 g, 0.15 mmol) and THE (5.0 mL) via cannula and the mixture was a stirred for 2 h. Ph$_2$PCl (3.3 g, 15.0 mmol) was added dropwise via cannula and the solution was heated to 70° C. for 3 h. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 2.56 g of [2,6-bis(2,6-dimethoxyphenyl)phenyl]-diphenylphosphine as a orange crystalline material), 48% yield.

Example 11. [2,6-Bis(2,6-dimethoxyphenyl)phenyl]-phenyl-isopropylphosphine

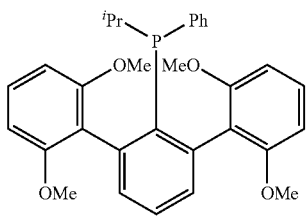 [SMILES: COc1cccc(OC)c1-c1cccc(-c2c(OC)cccc2OC)c1P(c1ccccc1)C(C)C]

To an oven-dried 100 mL flask, equipped with a magnetic stir bar and a condenser, and charged with magnesium (0.56 g, 23.0 mmol), ca. 1 mL of a solution of 2,6-dimethoxyiodobenzene (5.81 g, 22.0 mmol) in THF (15.0 mL) was added and heated. After the reaction was initiated, the rest solution was added dropwise and the reaction mixture was heated to reflux for 2 h to obtain a Grignard reagent. To another oven-dried two-neck 250 mL flask with THF (15 mL) and 1,3-dichlorobenzene (1.47 g, 10.0 mmol), 4.8 mL n-butyllithium (2.5 M solution in hexanes, 12.0 mmol) was added dropwise at −78° C. and stirred for 1 h. At that point the Grignard reagent was transferred via cannula to the solution, then warmed to room temperature, and the reaction solution was heated to 70° C. for 12 h. To a third oven-dried 100 mL flask, equipped with a magnetic stir bar and a condenser, with CuBr (1.72 g, 12.0 mmol), the above reaction solution was transferred via cannula and the mixture was a stirred for 20 min. PhPCl$_2$ (2.15 g, 12.0 mmol) was added dropwise via cannula and the solution was heated to 70° C. for 12 h. 4.0 mL $^i$PrMgBr (3.0 M solution in THF, 12.0 mmol) was added dropwise at −78° C. and the reaction solution was heated to 70° C. for 12 h. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 2.90 g of [2,6-bis(2,6-dimethoxyphenyl)phenyl]-phenyl-isopropylphosphine as a white crystalline material, 58% yield. m.p.: 153.2-154.9° C.

$^1$H NMR (400 MHz, CDCl$_3$) δ: 7.47 (t, J=7.5 Hz, 1H), 7.34 (ddd, J=18.9, 13.8, 6.7 Hz, 4H), 7.18 (d, J=7.4 Hz, 3H), 6.70 (d, J=8.3 Hz, 6H), 3.80 (s, 12H), 3.77 (s, 6H), 1.82 (s, 1H).

$^{13}$C NMR (101 MHz, CDCl$_3$) δ: 157.90, 157.68, 141.00, 136.99, 134.01, 129.75, 129.31, 129.22, 128.44, 127.52, 124.60, ° C. 87, 120.04, 109.60, 104.45, 104.32, 56.15, 55.96, 16.88.

$^{31}$P NMR (162 MHz, CDCl$_3$) δ: −13.29.

Example 12. [2,6-Bis(2,4,6-triisopropylphenyl)phenyl]-diphenylphosphine

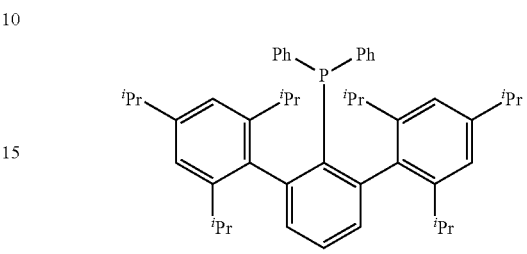

To an oven-dried 250 mL flask, equipped with a magnetic stir bar and a condenser, and charged with magnesium (0.67 g, 27.5 mmol), ca. 1 mL of a solution of 2,4,6-triisopropylbromobenzene (7.08 g, 25.0 mmol) in THF (10.0 mL) was added and heated. After the reaction was initiated, the rest solution was added dropwise and the reaction mixture was heated to reflux for 2 h to obtain a Grignard reagent. To another oven-dried two-neck 250 mL flask with THF (15 mL) and 1,3-dichlorobenzene (1.47 g, 10.0 mmol), n-butyllithium (5.0 mL of a 2.4 M solution in hexanes, 12.0 mmol) was added dropwise at −78° C. and stirred for 1 h. At that point the Grignard reagent was transferred via cannula to the solution, then warmed to room temperature, and the reaction solution was heated to 80° C. for 6 h. To a third oven-dried 250 mL flask, equipped with a magnetic stir bar and a condenser, and charged with CuBr (2.15 g, 15.0 mmol), the above reaction solution was transferred via cannula and the mixture was a stirred for 15 min. Then Ph$_2$PCl (3.31 g, 15.0 mmol) was added dropwise via cannula and the solution was heated to 70° C. for 6 h. Cooled to room temperature, 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 5.53 g of [2,6-bis(2,4,6-triisopropylphenyl)phenyl]-diphenylphosphine as a white crystalline material, 83% yield. m.p.: 148.4-149.6° C.

$^1$H NMR (400 MHz, CDCl$_3$) δ: 7.42 (t, J=7.5 Hz, 1H), 7.20 (dd, J=7.5, 2.2 Hz, 2H), 7.00 (t, J=6.9 Hz, 2H), 6.96-6.83 (m, 8H), 6.78 (s, 4H), 2.89-2.77 (m, 6H), 1.26 (d, J=6.9 Hz, 12H), 0.91 (dd, J=34.9, 6.7 Hz, 24H).

$^{13}$C NMR (101 MHz, CDCl$_3$) δ: 147.48, 147.26, 145.84, 138.05, 137.91, 137.27, 137.22, 134.65, 134.43, 132.29, 132.26, 127.64, 127.35, 127.31, 127.28, 120.51, 34.03, 30.91, 25.59, 24.03, 22.61.

$^{31}$P NMR (162 MHz, CDCl$_3$) δ: −5.89.

HR-MS m/z (%): Calcd for C$_{48}$H$_{60}$P [M$^+$+H] 667.4427; Found 667.4479 (100).

Example 13. [2,6-Bis(2,4,6-triisopropylphenyl)phenyl]-phenyl-cyclohexylphosphine

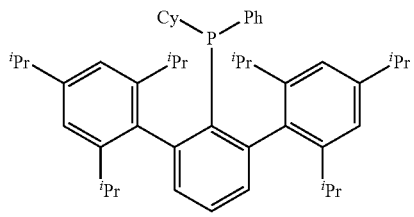

To an oven-dried 250 mL flask, equipped with a magnetic stir bar and a condenser, and charged with magnesium (0.67 g, 27.5 mmol), ca. 1 mL of a solution of 2,4,6-triisopropylbromobenzene (7.08 g, 25.0 mmol) in THF (10.0 mL) was added and heated. After the reaction was initiated, the rest solution was added dropwise and the reaction mixture was heated to reflux for 2 h to obtain a Grignard reagent. To another oven-dried two-neck 250 mL flask with THF (15 mL) and 1,3-dichlorobenzene (1.47 g, 10.0 mmol), n-butyllithium (5.0 mL of a 2.4 M solution in hexanes, 12.0 mmol) was added dropwise at −78° C. and stirred for 1 h. At that point the Grignard reagent was transferred via cannula to the solution, then warmed to room temperature, and the reaction solution was heated to 80° C. for 6 h. To a third oven-dried 250 mL flask, equipped with a magnetic stir bar and a condenser, and charged with CuBr (2.15 g, 15.0 mmol), the above reaction solution was transferred via cannula and the mixture was a stirred for 15 min. PhPCl$_2$ (2.68 g, 15.0 mmol) was added dropwise via cannula at −78° C. and the solution was heated to 70° C. for 6 h, 15.0 mL CyMgBr (1.0 M solution in THF, 15.0 mmol) was added dropwise at −78° C. and the reaction solution was heated to 70° C. for 12 h. Cooled to room temperature, 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 4.91 g of [2,6-bis(2,4,6-triisopropylphenyl)phenyl]-phenyl-cyclohexylphosphine as a white crystalline material, 73% yield. m.p.: 146.5-148.1° C.

$^1$H NMR (400 MHz, CDCl$_3$) δ: 7.36-7.30 (m, 1H), 7.15 (dd, J=7.6, 1.8 Hz, 3H), 7.06-6.96 (m, 6H), 6.88 (s, 2H), 2.97 (s, 4H), 2.69-2.60 (m, 2H), 1.34 (d, J=6.9 Hz, 17H), 1.29-1.20 (m, 1H), 1.02 (ddd, J=16.8, 13.2, 6.7 Hz, 27H), 0.89-0.78 (m, 2H).

$^{13}$C NMR (101 MHz, CDCl$_3$) δ: 147.80, 146.67, 146.52, 146.20, 146.05, 146.05, 138.10, 138.05, 135.25, 135.03, 132.04, 132.02, 127.75, 127.13, 127.05, 126.53, 120.84, 120.45, 34.23, 33.01, 32.68, 32.04, 31.91, 31.02, 30.95, 30.93, 30.68, 30.61, 26.86, 26.81, 26.74, 26.68, 25.98, 25.85, 24.21, 24.15, 22.58, 22.44.

$^{31}$P NMR (162 MHz, CDCl$_3$) δ: 6.72.

HR-MS m/z (%): Calcd for C$_{48}$H$_{66}$P [M$^+$+H] 673.4897; Found 673.4944 (100).

Example 14. [2,6-Bis(2,4,6-triisopropylphenyl)phenyl]-methyl-tert-butylphosphine (ZTPhos)

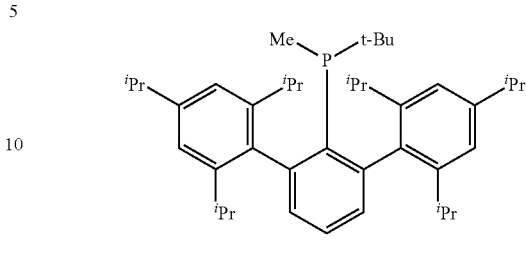

To an oven-dried 250 mL flask, equipped with a magnetic stir bar and a condenser, and charged with magnesium (0.56 g, 23.0 mmol), ca. 1 mL of a solution of 2,4,6-triisopropylbromobenzene (6.23 g, 22.0 mmol) in THF (10.0 mL) was added and heated. After the reaction was initiated, the rest solution was added dropwise and the reaction mixture was heated to reflux for 2 h to obtain a Grignard reagent. To another oven-dried two-neck 250 mL flask with THF (15 mL) and 1,3-dichlorobenzene (1.47 g, 10.0 mmol), n-butyllithium (4.8 mL of a 2.5 M solution in hexanes, 12.0 mmol) was added dropwise at −78° C. and stirred for 1 h. At that point the Grignard reagent was transferred via cannula to the solution, then warmed to room temperature, and the reaction solution was heated to 80° C. for 6 h. To a third oven-dried 250 mL flask, equipped with a magnetic stir bar and a condenser, and charged with CuBr (1.72 g, 12.0 mmol), the above reaction solution was transferred via cannula and the mixture was a stirred for 15 min. The mixture of $^t$BuPCl$_2$ (1.90 g, 12.0 mmol) and THF (5 mL) was added dropwise via cannula at −78° C. and the solution was heated to 70° C. for 6 h, 12.0 mL MeMgBr (1.0 M solution in THF, 12.0 mmol) was added dropwise at −78° C. and the reaction solution was warmed to room temperature for 12 h. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 3.09 g of [2,6-bis(2,4,6-triisopropylphenyl)phenyl]-methyl-tert-butylphosphine as a white crystalline material), 53% yield. m.p.: 145.3-146.7° C.

$^1$H NMR (400 MHz, CDCl$_3$) δ: 7.33-7.27 (m, 1H), 7.16 (d, J=7.5 Hz, 2H), 7.05 (d, J=5.9 Hz, 4H), 2.98 (dp, J=13.5, 6.5 Hz, 2H), 2.80 (ddq, J=26.6, 13.1, 6.6 Hz, 4H), 1.45-1.25 (m, 24H), 1.04 (dd, J=10.1, 6.8 Hz, 12H), 0.96 (d, J=7.0 Hz, 3H), 0.76 (t, J=14.2 Hz, 9H);

$^{13}$C NMR (101 MHz, CDCl$_3$) δ: 148.15, 147.96, 147.82, 146.22, 145.92, 139.18, 139.13, 137.37, 136.95, 131.90, 131.87, 126.54, 120.64, 120.09, 34.19, 31.02, 30.97, 30.95, 29.87, 29.68, 29.51, 29.35, 26.15, 25.83, 24.29, 24.05, 22.62, 8.33, 8.11;

$^{31}$P NMR (162 MHz, CDCl$_3$) δ: −3.33;

HR-MS m/z (%): Calcd for C$_{41}$H$_{62}$P [M$^+$+H] 585.4853; Found 585.4857 (100).

Example 15. [2,6-Bis(2,4,6-triisopropylphenyl)phenyl]-phenyl-isopropylphosphine

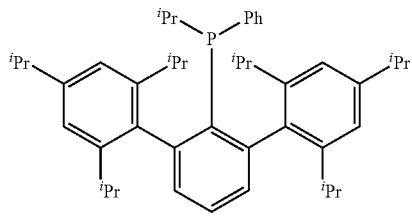 [SMILES: CC(C)c1cc(C(C)C)c(-c2cccc(-c3c(C(C)C)cc(C(C)C)cc3C(C)C)c2P(c2ccccc2)C(C)C)c(C(C)C)c1]

To an oven-dried 250 mL flask, equipped with a magnetic stir bar and a condenser, was charged with magnesium (0.56 g, 23.0 mmol), ca. 1 mL of a solution of 2,4,6-triisopropylbromobenzene (6.23 g, 22.0 mmol) in THE (10.0 mL) was added and heated. After the reaction was initiated, the rest solution was added dropwise and the reaction mixture was heated to reflux for 2 h to obtain a Grignard reagent. To another oven-dried two-neck 250 mL flask with THE (15 mL) and 1,3-dichlorobenzene (1.47 g, 10.0 mmol), 4.8 mL n-butyllithium (2.5 M solution in hexanes, 12.0 mmol) was added dropwise at −78° C. and stirred for 1 h. At that point the Grignard reagent was transferred via cannula to the solution, then warmed to room temperature, and the reaction solution was heated to 70° C. for 12 h. To a third oven-dried 250 mL flask, equipped with a magnetic stir bar and a condenser, and charged with CuBr (1.72 g, 12.0 mmol), the above reaction solution was transferred via cannula and the mixture was a stirred for 20 min. PhPCl$_2$ (2.15 g, 12.0 mmol) was added dropwise via cannula and the solution was heated to 70° C. for 12 h, 4.0 mL $^i$PrMgBr (3.0 M solution in THF, 12.0 mmol) was added dropwise at −78° C. and the reaction solution was heated to 70° C. for 12 h. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 3.98 g of [2,6-bis(2,4,6-triisopropylphenyl)phenyl]-phenyl-isopropylphosphine as a white crystalline material), 63% yield. m.p.: 144.3-146.2° C.

$^1$H NMR (400 MHz, CDCl$_3$) δ: 7.40-7.34 (m, 1H), 7.21 (d, J=7.0 Hz, 4H), 7.16-7.07 (m, 2H), 6.99 (t, J=9.5 Hz, 4H), 6.66 (s, 1H), 3.28-3.17 (m, 1H), 3.06 (s, 2H), 2.89 (s, 2H), 2.72-2.62 (m, 1H), 2.55 (s, 1H), 1.47-1.39 (m, 15H), 1.35 (d, J=6.9 Hz, 6H), 1.32 (d, J=6.8 Hz, 3H), 1.06 (d, J=6.6 Hz, 4H), 1.00-0.90 (m, 5H), 0.77 (d, J=6.7 Hz, 5H), 0.66 (dd, J=15.5, 6.7 Hz, 3H).

$^{31}$P NMR (162 MHz, CDCl$_3$) δ: −4.19.

HR-MS m/z (%): Calcd for C$_{45}$H$_{62}$P [M$^+$+H] 633.4583; Found 633.4580 (100).

Example 16. [2,6-Bis(2,4,6-triisopropylphenyl)phenyl]-dicyclohexylphosphine (XTPhos)

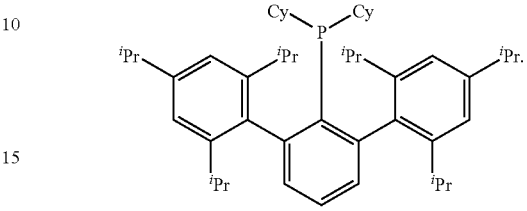

To an oven-dried 250 mL flask, equipped with a magnetic stir bar and a condenser, and charged with magnesium (0.56 g, 23.0 mmol), ca. 1 mL of a solution of 2,4,6-triisopropylbromobenzene (6.23 g, 22.0 mmol) in THE (10.0 mL) was added and heated. After the reaction was initiated, the rest solution was added dropwise and the reaction mixture was heated to reflux for 2 h to obtain a Grignard reagent. To another oven-dried two-neck 250 mL flask was added THE (15 mL) and 1,3-dichlorobenzene (1.47 g, 10.0 mmol), n-butyllithium (4.8 mL of a 2.5 M solution in hexanes, 12.0 mmol) was added dropwise at −78° C. and stirred for 2 h. At that point the Grignard reagent was transferred via cannula to the solution, then warmed to room temperature, and the reaction solution was heated to 70° C. for 12 h. To a third oven-dried 250 mL flask, equipped with a magnetic stir bar and a condenser, and charged with CuBr (1.72 g, 12.0 mmol), the above reaction solution was transferred via cannula and the mixture was a stirred for 15 min. Then a solution of Cy$_2$PCl (2.79 g, 12.0 mmol) in THE (5.0 mL) was added dropwise via cannula and the solution was heated to 70° C. for 6 h. Cooled to room temperature, 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 4.13 g of [2,6-bis(2,4,6-triisopropylphenyl)phenyl]-dicyclohexylphosphine as a white crystalline material), 61% yield. m.p.: 147.5-149.1° C.

$^1$H NMR (400 MHz, CDCl$_3$) δ: 7.30-7.25 (m, 1H), 7.14-7.12 (m, 1H), 7.11-7.10 (m, 1H), 7.07 (s, 4H), 3.01-2.92 (m, 2H), 2.84-2.72 (m, 4H), 1.83-1.71 (m, 3H), 1.63-1.53 (m, 5H), 1.48-1.40 (m, 5H), 1.36 (dd, J=11.7, 6.9 Hz, 24H), 1.22-1.15 (m, 2H), 1.11-1.04 (m, 2H), 1.00 (d, J=6.7 Hz, 13H), 0.89-0.81 (m, 4H).

$^{13}$C NMR (101 MHz, CDCl$_3$) δ: 147.55, 147.38, 145.70, 139.30, 139.25, 131.82, 131.79, 126.53, 120.79, 34.16, 34.06, 33.79, 31.92, 31.75, 30.74, 30.62, 30.50, 27.35, 27.27, 27.17, 27.01, 26.38, 25.98, 24.16, 23.12.

$^{31}$P NMR (162 MHz, CDCl$_3$) δ: 9.62, 9.52.

HR-MS m/z (%): Calcd for C$_{48}$H$_{72}$P [M$^+$+H] 679.5366; Found 679.5367 (100).

Example 17. [2,6-Bis(2,4,6-triisopropylphenyl)phenyl]-(2',6'-dimethoxy-2-biphenylyl)-methylphosphine

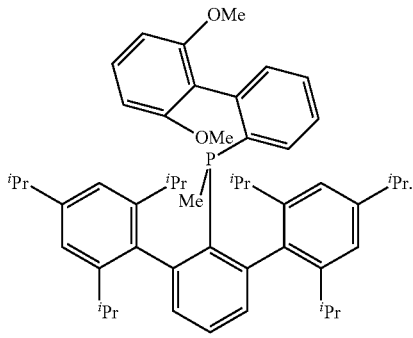 [SMILES: COc1cccc(OC)c1-c1ccccc1P(C)c1c(-c2c(C(C)C)cc(C(C)C)cc2C(C)C)cccc1-c1c(C(C)C)cc(C(C)C)cc1C(C)C]

To an oven-dried 250 mL flask, equipped with a magnetic stir bar and a condenser, was charged with magnesium (0.56 g, 23.0 mmol), ca. 1 mL of a solution of 2,4,6-triisopropylbromobenzene (6.23 g, 22.0 mmol) in THF (10.0 mL) was added and heated. After the reaction was initiated, the rest solution was added dropwise and the reaction mixture was heated to reflux for 2 h to obtain a Grignard reagent. To another oven-dried two-neck 250 mL flask with THF (15 mL) and 1,3-dichlorobenzene (1.47 g, 10.0 mmol), n-butyllithium (4.8 mL of a 2.5 M solution in hexanes, 12.0 mmol) was added dropwise at −78° C. and stirred for 2 h. At that point the Grignard reagent was transferred via cannula to the solution, then warmed to room temperature, and the reaction solution was heated to 70° C. for 12 h. Cooled to −78° C., PCl$_3$(1.65 g, 12.0 mmol) was added, warmed to room temperature for 6 h. To a third oven-dried 250 mL flask, equipped with a magnetic stir bar and a condenser, and charged with magnesium (0.39 g, 16.0 mmol), ca. 1 mL of a solution of 2',6'-dimethoxy-2-bromobiphenylyl (4.39 g, 15.0 mmol) in THF (12.0 mL) was added and heated. After the reaction was initiated, the rest solution was added dropwise and the reaction mixture was heated to reflux for 2 h to obtain a Grignard reagent. To a fourth oven-dried 250 mL flask, equipped with a magnetic stir bar and a condenser, and charged with CuCl (1.49 g, 15.0 mmol), the above reaction solution was transferred via cannula and the mixture was a stirred for 15 min. at −78° C. and the solution was heated to 70° C. for 6 h. 12.0 mL MeMgBr (1.0 M solution in THF, 12.0 mmol) was added dropwise at −78° C. and the reaction solution was heated to 70° C. for 12 h. 60 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 2.89 g of [2,6-bis(2,4,6-triisopropylphenyl)phenyl]-(2',6'-dimethoxy-2-biphenylyl)-methylphosphine as a white crystalline material, 39% yield.

$^{31}$P NMR (162 MHz, CDCl$_3$) δ. 7.12.

Example 18. [2,6-Bis(2-methoxy-1-naphthalenyl)phenyl]-diphenylphosphine

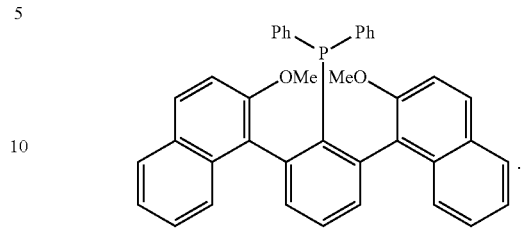

To an oven-dried 250 mL flask, equipped with a magnetic stir bar and a condenser, and charged with magnesium (0.67 g, 27.5 mmol), ca. 1 mL of a solution of 1-bromo-2-methoxynaphthalene (5.93 g, 25.0 mmol) in THF (10.0 mL) was added and heated. After the reaction was initiated, the rest solution was added dropwise and the reaction mixture was heated to reflux for 2 h to obtain a Grignard reagent. To another oven-dried two-neck 250 mL flask with THF (15 mL) and 1,3-dichlorobenzene (1.47 g, 10.0 mmol), n-butyllithium (5.0 mL of a 2.4 M solution in hexanes, 12.0 mmol) was added dropwise at −78° C. and stirred for 2 h. At that point the Grignard reagent was transferred via cannula to the solution, then warmed to room temperature, and the reaction solution was heated to 70° C. for 12 h. Then added the mixture of Pd(PPh$_3$)$_4$ (0.17 g, 0.15 mmol) and THF (5.0 mL) via cannula and the mixture was a stirred for 20 min at room temperature. Ph$_2$PCl (3.3 g, 15.0 mmol) was added dropwise at −78° C. and the solution was heated to 70° C. for 6 h. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 3.05 g of [2,6-bis(2-methoxy-1-naphthalenyl)phenyl]-diphenylphosphine as a white crystalline material, 53% yield. m.p.: 153.2-155.0° C.

$^1$H NMR (400 MHz, CDCl$_3$) δ: 7.72-7.57 (m, 5H), 7.42 (dd, J=7.5, 5.7 Hz, 4H), 7.30 (ddd, J=7.4, 4.5, 2.5 Hz, 4H), 7.06-6.98 (m, 2H), 6.90-6.77 (m, 6H), 6.72 (t, J=7.4 Hz, 4H), 3.55 (d, J=4.4 Hz, 6H).

$^{13}$C NMR (101 MHz, CDCl$_3$) δ: 154.07, 143.67, 143.51, 136.63, 136.39, 136.20, 136.07, 134.03, 133.71, 133.50, 132.14, 132.12, 129.27, 128.51, 127.73, 126.76, 126.44, 126.36, 126.06, 125.46, 124.77, 124.72, 122.98, 112.16, 55.26.

$^{31}$P NMR (162 MHz, CDCl$_3$) δ: −4.54.

HR-MS m/z (%): Calcd for C$_{40}$H$_{32}$O$_2$P [M$^+$+H] 575.2134; Found 575.2151 (100).

Example 19. [2,6-Bis(2-methoxy-1-naphthalenyl)phenyl]-dicyclohexylphosphine

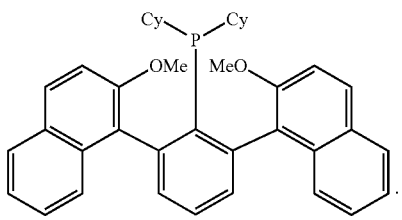

To an oven-dried 250 mL flask, equipped with a magnetic stir bar and a condenser, was charged with magnesium (0.56 g, 23.0 mmol), ca. 1 mL of a solution of 1-bromo-2-methoxynaphthalene (5.22 g, 22.0 mmol) in THF (10.0 mL) was added and heated. After the reaction was initiated, the rest solution was added dropwise and the reaction mixture was heated to reflux for 2 h to obtain a Grignard reagent. To another oven-dried two-neck 250 mL flask with THE (15 mL) and 1,3-dichlorobenzene (1.47 g, 10.0 mmol), n-butyl-lithium (5.0 mL of a 2.4 M solution in hexanes, 12.0 mmol) was added dropwise at −78° C. and stirred for 2 h. At that point the Grignard reagent was transferred via cannula to the solution, then warmed to room temperature, and the reaction solution was heated to 70° C. for 12 h. To a third oven-dried 250 mL flask, equipped with a magnetic stir bar and a condenser, and charged with CuBr (1.72 g, 12.0 mmol), the reaction mixture was transferred via cannula to the flask was stirred for 20 min. Then a solution of $Cy_2PCl$ (2.79 g, 12.0 mmol) in THE (5.0 mL) was added dropwise via cannula and the solution was heated to 70° C. for 6 h. Cooled to room temperature, 40 mL of ammonia (26.0%-28.0%) was added and stirred for 30 min, then the mixture was extracted with dichloromethane (3×50 mL), and the combined organic phase was added with brine, dried over anhydrous sodium sulfate and concentrated in vacuo to give a light yellow oil. The residue was purified by column chromatography to give 2.58 g of [2,6-bis(2-methoxy-1-naphthalenyl)phenyl]-dicyclohexylphosphine as a white crystalline material, 44% yield. m.p.: 156.3-157.6° C.

$^1$H NMR (400 MHz, $CDCl_3$) δ: 7.94 (d, J=9.0 Hz, 2H), 7.86 (d, J=7.8 Hz, 2H), 7.43-7.33 (m, 8H), 7.27 (d, J=8.0 Hz, 3H), 3.98-3.90 (m, 6H), 1.48-1.19 (m, 11H), 0.95-0.41 (m, 11H).

$^{13}$C NMR (101 MHz, $CDCl_3$) δ: 153.59, 144.78, 144.62, 139.65, 139.34, 134.59, 131.61, 131.57, 128.87, 128.69, 128.40, 127.80, 127.15, 127.10, 126.06, 125.81, 112.86, 57.01, 56.03, 33.11, 32.95, 32.93, 32.71, 31.55, 31.38, 29.74, 27.07, 27.01, 26.94, 26.91, 26.35.

$^{31}$P NMR (162 MHz, $CDCl_3$) δ: 9.76.

HR-MS m/z (%): Calcd for $C_{40}H_{43}P$ [M] 586.2995; Found 586.2965 (100).

Example 20. [2,6-Bis(2-methoxy-1-naphthalenyl)phenyl]-(4-dimethylamino-phenyl)-cyclohexylphosphine

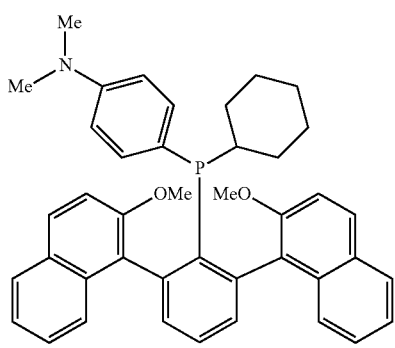 [SMILES: COc1ccc2ccccc2c1-c1cccc(-c2c(OC)ccc3ccccc23)c1P(c1ccc(N(C)C)cc1)C1CCCCC1]

To an oven-dried 250 mL flask, equipped with a magnetic stir bar and a condenser, and charged with magnesium (0.67 g, 27.5 mmol), ca. 1 mL of a solution of 1-bromo-2-methoxynaphthalene (5.93 g, 25.0 mmol) in THE (10.0 mL) was added and heated. After the reaction was initiated, the rest solution was added dropwise and the reaction mixture was heated to reflux for 2 h to obtain a Grignard reagent. To another oven-dried two-neck 250 mL flask with THE (15 mL) and 1,3-dichlorobenzene (1.47 g, 10.0 mmol), n-butyl-lithium (5.0 mL of a 2.4 M solution in hexanes, 12.0 mmol) was added dropwise at −78° C. and stirred for 2 h. At that point the Grignard reagent was transferred via cannula to the solution, then warmed to room temperature, and the reaction solution was heated to 70° C. for 12 h. To a third oven-dried 250 mL flask, equipped with a magnetic stir bar and a condenser, and charged with CuCl (1.20 g, 12.0 mmol), the reaction mixture was transferred via cannula to the flask was stirred for 20 min. Cooled to −78° C., then a solution of $CyPCl_2$ (2.22 g, 12.0 mmol) in THE (5.0 mL) was added dropwise via cannula and the solution was heated to 40° C. for 6 h. Cooled to −50° C., a solution of magnesium 4-dimethylaminophenyl bromide in THE (24.0 mmol) was added dropwise via cannula and the solution was heated to 70° C. for 6 days. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 2.84 g of [2,6-bis(2-methoxy-1-naphthalenyl)phenyl]-(4-dimethylamino-phenyl)-cyclohexylphosphine as an orange crystalline material, 45% yield. m.p.: 157.2-158.9° C.

$^1$H NMR (400 MHz, $CDCl_3$) δ: 7.93 (dd, J=8.9, 6.3 Hz, 3H), 7.77-7.69 (m, 1H), 7.57-7.51 (m, 3H), 7.44 (d, J=9.1 Hz, 2H), 7.29-7.24 (m, 2H), 7.20-7.13 (m, 2H), 7.10-7.05 (m, 1H), 7.02-6.98 (m, 1H), 6.28 (s, 2H), 5.98 (d, J=8.0 Hz, 2H), 4.01 (s, 3H), 3.76 (s, 3H), 2.80 (s, 6H), 2.11-2.00 (m, 1H), 1.82-1.54 (m, 4H), 1.48-1.17 (m, 4H), 1.11-0.86 (m, 3H).

$^{13}$C NMR (101 MHz, $CDCl_3$) δ: 153.76, 153.74, 153.59, 149.15, 145.11, 144.86, 144.02, 143.93, 138.73, 138.42, 134.59, 134.42, 134.40, 134.28, 134.07, 132.03, 132.01, 131.36, 131.31, 129.10, 128.82, 128.72, 128.71, 128.47, 127.95, 126.99, 126.22, 126.16, 125.98, 125.50, ° C. 07, 122.81, 120.29, 120.18, 112.57, 112.49, 111.56, 111.49, 56.27, 55.34, 50.80, 40.37, 32.13, 32.06, 30.36, 30.19, 30.14, 26.94, 26.84, 26.71, 26.60.

$^{31}$P NMR (162 MHz, $CDCl_3$) δ: −9.15.

HR-MS m/z (%): Calcd for $C_{42}H_{42}NO_2P$ [M] 623.2947; Found 623.2930 (100).

Example 21. [2,6-Bis(2-methoxy-1-naphthyl)phenyl]-bis(3,5-bis(trifluoromethyl) phenyl]phosphine

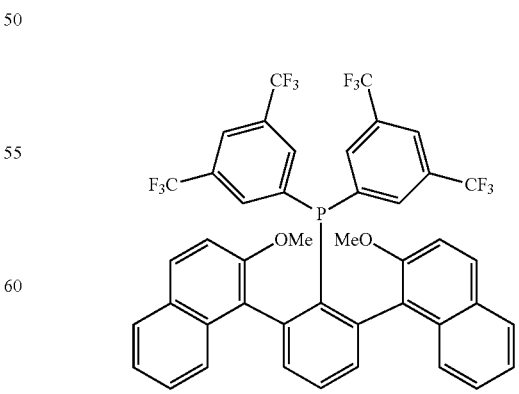

To an oven-dried 250 mL flask, equipped with a magnetic stir bar and a condenser, and charged with magnesium (0.29 g, 12.0 mmol), ca. 1 mL of a solution of 1-bromo-2-methoxynaphthalene (2.61 g, 11.0 mmol) in THF (5.0 mL) was added and heated. After the reaction was initiated, the rest solution was added dropwise and the reaction mixture was heated to reflux for 2 h to obtain a Grignard reagent. To another oven-dried two-neck 250 mL flask with THF (15 mL) and 1,3-dichlorobenzene (0.74 g, 5.0 mmol), n-butyllithium (2.4 mL of a 2.5 M solution in hexanes, 6.0 mmol) was added dropwise at −78° C. and stirred for 2 h. At that point the Grignard reagent was transferred via cannula to the solution, then warmed to room temperature, and the reaction solution was heated to 70° C. for 12 h. To a third oven-dried 250 mL flask, equipped with a magnetic stir bar and a condenser, and charged with CuCl (0.6 g, 6.0 mmol), the reaction mixture was transferred via cannula to the flask was stirred for 20 min. Cooled to −78° C., then (3,5-ditrifluoromethylphenyl)$_2$PCl was added dropwise via cannula and the solution was warmed to room temperature and heated to reflux for 6 h. 50 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 2.03 g of [2,6-Bis(2-methoxy-1-naphthyl)phenyl]-bis[(3,5-bis(trifluoromethyl)phenyl]phosphine as a white crystalline material, 48% yield. m.p.: 151.1-152.6° C.

$^1$H NMR (400 MHz, CDCl$_3$) δ: 7.77-7.69 (m, 5H), 7.55-7.49 (m, 2H), 7.45-7.42 (m, 4H), 7.41 (d, J=2.7 Hz, 1H), 7.40-7.38 (m, 1H), 7.38-7.36 (m, 1H), 7.35 (d, J=1.2 Hz, 1H), 7.33 (d, J=6.9 Hz, 4H), 7.08 (d, J=9.1 Hz, 2H), 3.68 (s, 6H).

$^{13}$C NMR (101 MHz, CDCl$_3$) δ: 154.29, 143.38, 143.22, 138.54, 138.35, 133.63, 133.01, 132.78, 132.57, 132.54, 130.76, 130.25, 128.36, 128.02, 127.00, 124.57, ° C. 78, 121.82, 121.75, 112.56, 55.60, 1.11.

$^{31}$P NMR (162 MHz, CDCl$_3$) δ: −3.12.

HR-MS m/z (%): Calcd for $C_{44}H_{27}F_{12}O_2P$ [M] 846.1552; Found 846.1552(100).

Example 22. [2,6-Bis(2-methoxy-6-dimethylaminophenyl)phenyl]-diphenylphosphine

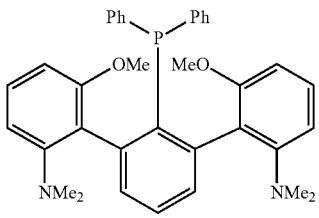 [SMILES: COc1cccc(N(C)C)c1-c1cccc(-c2c(OC)cccc2N(C)C)c1P(c1ccccc1)c1ccccc1]

To an oven-dried 250 mL flask, equipped with a magnetic stir bar and a condenser, and charged with magnesium (0.56 g, 23.0 mmol), ca. 1 mL of a solution of 2-methoxy-6-dimethylaminoliodobenzene (6.10 g, 22.0 mmol) in THF (10.0 mL) was added and heated. After the reaction was initiated, the rest solution was added dropwise and the reaction mixture was heated to reflux for 2 h to obtain a Grignard reagent. To another oven-dried two-neck 250 mL flask with THF (15 mL) and 1,3-dichlorobenzene (1.47 g, 10.0 mmol), n-butyllithium 4.8 mL of a 2.5 M solution in hexanes, 12.0 mmol) was added dropwise at −78° C. and stirred for 2 h. At that point the Grignard reagent was transferred via cannula to the solution, then warmed to room temperature, and the reaction solution was heated to 70° C. for 12 h. To a third oven-dried 250 mL flask, equipped with a magnetic stir bar and a condenser, and charged with CuCl (0.6 g, 6.0 mmol), the reaction mixture was transferred via cannula to the flask was stirred for 15 min. Cooled to −78° C. Then Ph$_2$PCl (2.65 g, 12.0 mmol) was added dropwise via cannula and the solution was warmed to room temperature and stirred for 6 h. 50 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 1.57 g of [2,6-Bis(2-methoxy-6-dimethylaminophenyl) phenyl]-diphenylphosphine as a white crystalline material, 28% yield.

$^1$H NMR (400 MHz, CDCl$_3$) δ: 7.73-7.62 (m, 3H), 7.35-7.27 (m, 7H), 7.19-7.12 (m, 3H), 6.41-6.28 (m, 6H), 3.80 (s, 6H), 2.94 (s, 12H).

$^{31}$P NMR (162 MHz, CDCl$_3$) δ: −13.62, −13.66.

Example 23. [2,6-Bis(2,4,6-triisopropylphenyl)phenyl]-bis(2-thienyl)phosphine

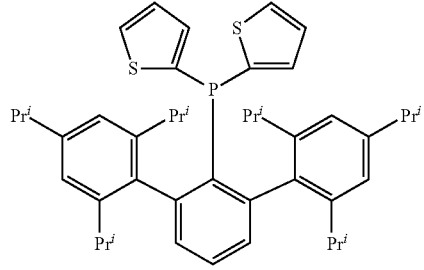

To an oven-dried 250 mL flask, equipped with a magnetic stir bar and a condenser, and charged with magnesium (0.56 g, 23.0 mmol), ca. 1 mL of a solution of 2,4,6-triisopropylbromobenzene (6.23 g, 22.0 mmol) in THF (10.0 mL) was added and heated. After the reaction was initiated, the rest solution was added dropwise and the reaction mixture was heated to reflux for 2 h to obtain a Grignard reagent. To another oven-dried two-neck 250 mL flask with THF (15 mL) and 1,3-dichlorobenzene (1.47 g, 10.0 mmol), n-butyllithium (4.8 mL of a 2.5 M solution in hexanes, 12.0 mmol) was added dropwise at −78° C. and stirred for 2 h. At that point the Grignard reagent was transferred via cannula to the solution, then warmed to room temperature, and the reaction solution was heated to 70° C. for 12 h. Cooled to −78° C., PCl$_3$ (1.65 g, 12.0 mmol) was added, warmed to room temperature for 6 h. To third 250 mL flask, equipped with a magnetic stir bar and a condenser, was charged with magnesium (0.90 g, 37.0 mmol), ca. 1 mL of a solution of 2-bromine thiophene (5.87 g, 36.0 mmol) in THF (15.0 mL) was added and heated. After the reaction was initiated, the rest solution was added dropwise and the reaction mixture was heated to reflux for 2 h to obtain a Grignard reagent. To a fourth oven-dried 250 mL flask, equipped with a magnetic stir bar and a condenser, and charged with CuCl (1.19 g, 12.0 mmol), the reaction mixture was transferred via cannula to the flask was stirred for 15 min. Cooled to −78° C. Then Grignard reagent of 2-bromine thiophene was added dropwise via cannula and the solution was heated to 70° C. for 12 h. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 3.59 g of [2,6-bis(2,4,6-triisopropylphenyl)phenyl]-bis(2-thienyl)phosphine as a blue crystalline material, 53% yield. m.p.: 144.3-145.5° C.

$^1$H NMR (400 MHz, CDCl$_3$) δ: 7.47-7.40 (m, 1H), 7.26-7.23 (m, 2H), 7.23-7.18 (m, 2H), 6.88 (s, 4H), 6.79-6.75 (m, 2H), 6.75-6.70 (m, 2H), 2.85 (s, 6H), 1.30 (d, J=6.9 Hz, 12H), 1.04-0.92 (m, 24H).

$^{13}$C NMR (101 MHz, CDCl$_3$) δ: 147.80, 146.63, 146.45, 146.19, 146.18, 139.55, 139.29, 136.76, 136.70, 135.63, 135.40, 135.20, 134.96, 132.31, 132.28, 131.55, 131.52, 127.93, 126.69, 126.63, 120.64, 34.17, 31.13, 25.58, 24.09, 22.70.

$^{31}$P NMR (162 MHz, CDCl$_3$) δ: −33.31.

HR-MS m/z (%): Calcd for C$_{44}$H$_{56}$S$_2$P [M$^+$+H] 679.3555; Found 679.3560(100).

Example 24. [2,6-Bis(2,6-dimethoxyphenyl)phenyl]-dicyclohexylphosphine (STPhos)

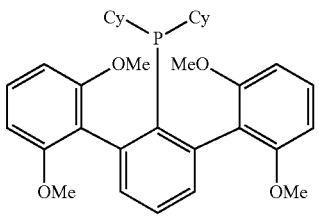

To an oven-dried 100 mL flask, equipped with a magnetic stir bar and a condenser, and charged with magnesium (0.67 g, 27.5 mmol), ca. 1 mL of a solution of 2,6-dimethoxybromobenzene (5.40 g, 25.0 mmol) in THF (10.0 mL) was added and heated. After the reaction was initiated, the rest solution was added dropwise and the reaction mixture was heated to reflux for 2 h to obtain a Grignard reagent. To another oven-dried two-neck 250 mL flask with THF (15 mL) and 1,3-dichlorobenzene (1.47 g, 10.0 mmol), n-butyllithium (4.8 mL of a 2.5 M solution in hexanes, 12.0 mmol) was added dropwise at −78° C. and stirred for 2 h. At that point the Grignard reagent was transferred via cannula to the solution, then warmed to room temperature, and the reaction solution was heated to 70° C. for 12 h. Cooled to −78° C. A mixture of CyPCl$_2$ (2.68 g, 15.0 mmol) and THF (5.0 mL) was added dropwise via cannula and the solution was heated to 70° C. for 6 h. Then CyMgCl (15.0 mL of a 1.0 M in THF, 15.0 mmol) and mixture of CuCl (1.49 g, 15.0 mmol) and THF (10.0 mL) was added dropwise at −78° C. and the reaction solution was heated to 70° C. for 12 h. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 0.87 g of [2,6-bis(2,6-dimethoxyphenyl)phenyl]-dicyclohexylphosphine as a white crystalline material, 16% yield.

$^1$H NMR (400 MHz, CDCl$_3$) δ: 7.38 (t, J=7.5 Hz, 1H), 7.35-7.28 (m, 2H), 7.06 (dd, J=7.5, 1.1 Hz, 2H), 6.61 (dd, J=8.2, 4.2 Hz, 4H), 3.72 (s, 12H), 1.70-1.48 (m, 12H), 1.33 (d, J=11.8 Hz, 2H), 1.12-0.78 (m, 10H).

$^{13}$C NMR (101 MHz, CDCl$_3$) δ: 157.74, 142.25, 142.09, 137.92, 137.62, 130.98, 130.95, 128.25, 127.72, 121.92, 121.86, 103.12, 55.38, 33.70, 33.54, 32.38, 32.17, 31.98, 31.80, 27.64, 27.52, 27.44, 27.33, 26.67.

$^{31}$P NMR (162 MHz, CDCl$_3$) δ: 11.34.

Example 25. [2,6-Bis(2,4,6-triisopropylphenyl)phenyl]-bis[3,5-bis(trifluoromethyl)-phenyl]phosphine

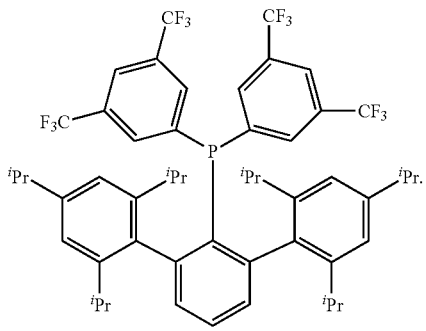 [SMILES: CC(C)c1cc(C(C)C)c(-c2cccc(-c3c(C(C)C)cc(C(C)C)cc3C(C)C)c2P(c2cc(C(F)(F)F)cc(C(F)(F)F)c2)c2cc(C(F)(F)F)cc(C(F)(F)F)c2)c(C(C)C)c1]

To an oven-dried 250 mL flask, equipped with a magnetic stir bar and a condenser, and charged with magnesium (0.56 g, 23.0 mmol), ca. 1 mL of a solution of 2,4,6-triisopropylbromobenzene (6.23 g, 22.0 mmol) in THF (10.0 mL) was added and heated. After the reaction was initiated, the rest solution was added dropwise and the reaction mixture was heated to reflux for 2 h to obtain a Grignard reagent. To another oven-dried two-neck 250 mL flask with THF (15 mL) and 1,3-dichlorobenzene (1.47 g, 10.0 mmol), n-butyllithium (4.8 mL of a 2.5 M solution in hexanes, 12.0 mmol) was added dropwise at −78° C. and stirred for 2 h. At that point the Grignard reagent was transferred via cannula to the solution, then warmed to room temperature, and the reaction solution was heated to 70° C. for 12 h. Cooled to −78° C., PCl$_3$ (1.65 g, 12.0 mmol) was added, warmed to room temperature for 6 h. To an third 250 mL flask, equipped with a magnetic stir bar and a condenser, and charged with magnesium (0.39 g, 16.0 mmol), ca. 1 mL of a solution of 3,5-bistrifluoromethylbromobenzene (4.40 g, 15.0 mmol) in THF (10.0 mL) was added and heated. After the reaction was initiated, the rest solution was added dropwise and the reaction mixture was heated to reflux for 2 h to obtain a Grignard reagent. To a fourth oven-dried 250 mL flask, equipped with a magnetic stir bar and a condenser, and charged with CuCl (1.48 g, 15.0 mmol), the above reaction solution was transferred via cannula and the mixture was a stirred for 30 min. The rest solution was added dropwise via cannula at −78° C. and the solution was heated to 70° C. for 12 h. 40 mL of ammonia (26.0%-28.0%) was added and stirred for 30 min, then the mixture was extracted with dichloromethane (3×50 mL), and the combined organic phase was washed with brine, dried over anhydrous sodium sulfate and concentrated in vacuo to give a light yellow oil. The residue was purified by column chromatography to give 4.03 g of [2,6-bis(2,4,6-triisopropylphenyl)-phenyl-bis[3,5-bis(trifluoromethyl)-phenyl]phosphine a white crystalline material, 43% yield. m.p.: 139.7-141.2° C.

$^1$H NMR (400 MHz, CDCl$_3$) δ: 8.03 (s, 2H), 7.80 (d, J=7.0 Hz, 4H), 7.48-7.37 (m, 1H), 7.22 (d, J=7.4 Hz, 2H), 7.10 (d, J=8.5 Hz, 4H), 3.05-2.92 (m, 2H), 2.82-2.72 (m,

1H), 2.67-2.55 (m, 3H), 1.40-1.34 (m, 12H), 1.20 (t, J=6.0 Hz, 11H), 1.16 (t, J=6.1 Hz, 11H), 1.10 (s, 1H), 1.08 (s, 1H).

$^{13}$C NMR (101 MHz, CDCl$_3$) δ: 148.30, 146.47, 145.92, 142.38, 137.48, 137.31, 136.54, 133.37, 133.34, 133.19, 133.12, 129.78, 128.49, 127.84, 126.50, 124.46, 124.42, 124.38, 124.08, 121.36, 120.69, 120.43, 34.28, 34.19, 30.89, 30.40, 29.73, 24.65, 24.30, 24.11, 24.08, 24.05, 23.51.

$^{31}$P NMR (162 MHz, CDCl$_3$) δ: −4.15.

Example 26. Trans-dichloro{bis[2,6-bis(2-methoxyphenyl)phenyl-diphenylphosphine]palladium(II)}

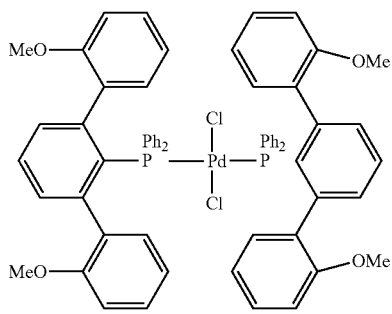

In an inert atmosphere, a 50 mL Shlenk bottle was charged with [2,6-bis(2-methoxyphenyl)phenyl]-diphenylphosphine (240.0 mg, 0.5 mmol) and di(acetonitrile) palladium chloride (65.0 mg, 0.25 mmol), and 5 mL of dichloromethane and the mixture was a stirred for 6 h. The solvent was a removed in vacuum and The residue was purified by recrystallization in methanol to give trans-dichloro{bis[2,6-bis(2-methoxyphenyl)phenyl-diphenylphosphine]palladium(II)} as a yellow solid (0.23 g, 77%).

$^1$H NMR (500 MHz, DMSO) δ: 7.50-7.44 (m, 1H), 7.25-7.17 (m, 3H), 7.15-7.13 (m, 1H), 7.11-6.96 (m, 12H), 6.91-6.85 (m, 2H), 6.74-6.63 (m, 2H), 6.52-6.46 (m, 2H), 3.59 (s, 3H), 3.38 (s, 3H).

$^{31}$P NMR (162 MHz, DMSO) δ: 30.94.

Example 27. Bis[(2,6-diphenyl-4-methylphenyl)-diphenylphosphine]palladium(0)

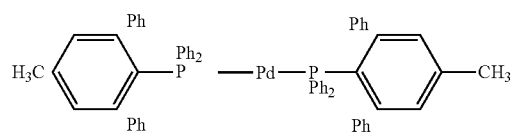

In an inert atmosphere, a 50 mL Shlenk bottle was a charged with (2,6-diphenyl-4-methylphenyl)-diphenylphosphine (236 mg, 0.55 mmol) and Me$_2$Pd(II)(TMEDA) (67 mg, 0.25 mmol), and 2 mL of dichloromethane and the mixture was a stirred for 6 h. The solvent was a removed in vacuum and the residue was purified by recrystallization in acetone to give bis[(2,6-diphenyl-4-methylphenyl)-diphenylphosphine]palladium(0) as black solid (0.21 g, 70%).

$^{31}$P NMR (162 MHz, CDCl$_3$) δ: 26.04.

Example 28. Chloro[(2,6-diphenyl-4-methylphenyl)-diphenylphosphine-(N,N-dimethylbenzylamine-2-)palladium(II)]

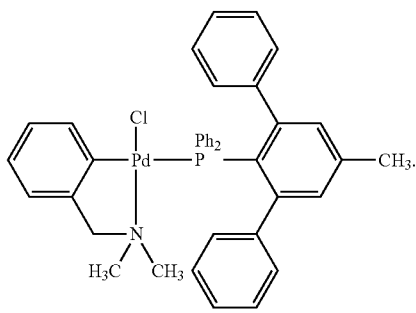

In an inert atmosphere, a 50 mL Shlenk bottle was a charged with (2,6-diphenyl-4-methylphenyl)-diphenylphosphine (214.0 mg, 0.5 mmol) and chloro (N,N-dimethylbenzylamine-2-)palladium(II)(II) dimer(138.0 mg, 0.25 mmol), and 5 mL of dichloromethane and the mixture was a stirred for 6 h. The solvent was a removed in vacuum and the residue was purified by a short column (dichloromethane) to afford chloro[(2,6-diphenyl-4-methylphenyl)-diphenylphosphine-(N,N-dimethylbenzylamine-2-)palladium(II)] as a yellow solid (0.31 g, 90%).

$^1$H NMR (400 MHz, CDCl$_3$) δ: 7.50-7.33 (m, 5H), 7.12-7.02 (m, 3H), 7.02-6.94 (m, 3H), 6.94-6.90 (m, 3H), 6.89 (s, 2H), 6.88-6.86 (m, 1H), 6.85 (d, J=3.1 Hz, 3H), 6.74-6.67 (m, 2H), 6.17-6.10 (m, 1H), 5.55-5.49 (m, 1H), 3.99 (d, J=1.2 Hz, 2H), 2.91 (d, J=2.4 Hz, 6H), 2.30 (s, 3H).

$^{13}$C NMR (101 MHz, CDCl$_3$) δ: 149.05, 148.20, 148.18, 146.75, 146.67, 142.78, 142.74, 138.48, 138.46, 137.52, 137.42, 137.14, 137.03, 132.81, 132.73, 131.34, 130.86, 129.44, 129.41, 127.25, 127.14, 126.19, 124.38, 124.32, 123.56, 122.08, 50.63, 50.61, 29.72, 20.89.

$^{31}$P NMR (162 MHz, CDCl$_3$) δ: 42.51.

HR-MS m/z (%): Calcd for C$_{40}$H$_{37}$NPPd [M$^+$-Cl] 668.1708; Found 668.1755(100).

Example 29. Chloro{(2,6-diphenyl-4-methylphenyl)diphenylphosphine-[2-(2-aminoethyl)phenyl]}palladium(II)

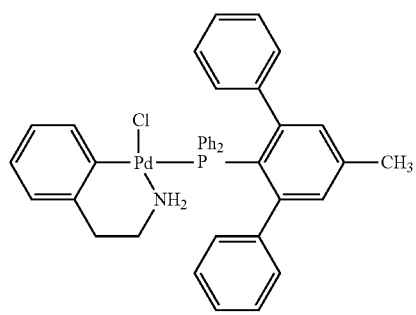

In an inert atmosphere, a 50 mL Shlenk bottle was a charged with (2,6-diphenyl-4-methylphenyl)diphenylphosphine (214.0 mg, 0.5 mmol) and chloro [2-(2-aminoethyl)phenyl] palladium(II) dimer (130.0 mg, 0.25 mmol), and 10 mL of dichloromethane and the mixture was a stirred for 6 h. The solvent was a removed in vacuum and the residue was purified by a short column (dichloromethane) to afford chloro{(2,6-diphenyl-4-methylphenyl)diphenylphosphine-[2-(2-aminoethyl)phenyl]}palladium(II) as a yellow solid (0.27 g, 80%).

$^{1}$H NMR (400 MHz, CDCl$_{3}$) δ: 8.06-7.95 (m, 1H), 7.76-7.69 (m, 1H), 7.64-7.30 (m, 12H), 7.21-7.10 (m, 4H), 7.08-6.91 (m, 4H), 6.65-6.58 (m, 2H), 6.56-6.50 (m, 1H), 6.49-6.42 (m, 2H), 2.46-2.40 (m, 3H), 1.58-1.52 (m, 4H), 1.47-1.44 (m, 2H).

$^{31}$P NMR (162 MHz, CDCl$_{3}$) δ: 22.69.

Example 30. Methanesulfonato{[2,6-bis(2,4,6-triisopropylphenyl)phenyl-dicyclohexylphosphine](2'-amino-1,1'-biphenyl-2-yl)palladium(II)}

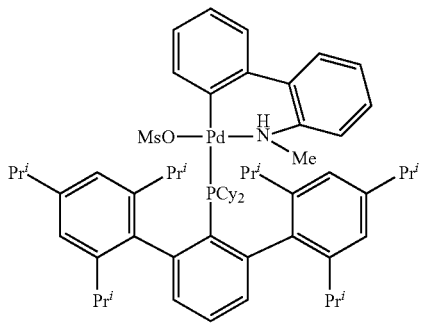

In an inert atmosphere, a 50 mL Shlenk bottle was a charged with 2,6-bis(2,4,6-triisopropylphenyl)phenyl-dicyclohexylphosphine (271.0 mg, 0.4 mmol) and methanesulfonato-2'-amino-1,1'-biphenyl-2-yl)palladium(II) dimer (148.0 mg, 0.2 mmol), and 5 mL of dichloromethane and the mixture was a stirred for 6 h. The solvent was a removed in vacuum and the residue was purified by a short column (dichloromethane) to afford methanesulfonato{[2,6-bis(2,4,6-triisopropylphenyl)phenyl-dicyclohexylphosphine](2'-amino-1,1'-biphenyl-2-yl)palladium(II)} as yellow solid (0.37 g, 89%). $^{31}$P NMR (162 MHz, CDCl$_{3}$) δ: 59.07, 25.02.

Example 31. [(TXPhos)(allyl)PdCl]

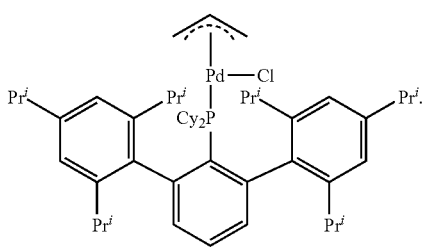

In an inert atmosphere, a 50 mL Shlenk bottle was a charged with 2,6-bis(2,4,6-triisopropylphenyl)phenyl-dicyclohexylphosphine (135.0 mg, 0.2 mmol) and allyl palladium(II) chloride dimer (36.0 mg, 0.1 mmol), and 3 mL of dichloromethane and the mixture was a stirred for 6 h. The solvent was a removed in vacuum and the residue was purified by a short column (dichloromethane) to afford a yellow solid (0.15 g, 90%).

$^{31}$P NMR (162 MHz, CDCl$_{3}$) δ: 67.00.

Example 32-38

TABLE 1

The aminations of 4-Chloroanisole with Diphenylamine; XTPhos(example-16) as the ligand [a]

| Example | Base | Tem. (° C.) | Solvent | Pd Source (mol %) | P:Pd | Time (h) | yield (%) |
|---|---|---|---|---|---|---|---|
| 32 | NaO$^{t}$Bu | 100 | toluene | [PdCl(π-allyl)]$_{2}$ (0.25) | 1:1 | 6 | 99 |
| 33 | NaO$^{t}$Bu | 100 | toluene | [PdCl(π-allyl)]$_{2}$ (0.25) | 2:1 | 6 | 98 |
| 34 | NaO$^{t}$Bu | 100 | toluene | [PdCl(π-allyl)]$_{2}$ (0.25) | 3:1 | 6 | 98 |
| 35 | NaO$^{t}$Bu | 100 | toluene | [PdCl(π-allyl)]$_{2}$ (0.05) | 1:1 | 12 | 50 |
| 36 | NaO$^{t}$Bu | 100 | toluene | [PdCl(π-allyl)]$_{2}$ (0.05) | 2:1 | 12 | 90 |
| 37 | NaO$^{t}$Bu | 100 | toluene | [PdCl(π-allyl)]$_{2}$ (0.05) | 3:1 | 12 | 73 |
| 38[b] | CH$_{3}$MgCl | 145 | xylene | [PdCl(π-allyl)]$_{2}$ (0.05) | 2:1 | 1 | 86 |

XTPhos:

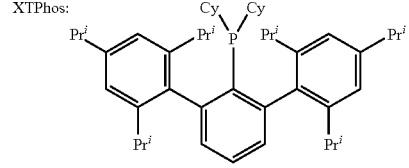

[a] In glove box, a mixture of aryl halide (1.1 mmol), diphenylamine (1.0 mmol), dodecane (130 uL, 0.57 mmol), NaOtBu (115 mg, 1.2 mmol), moderate of the ligand and Pd Source was taken in pressure tubing and heated at 100° C. The organic phase was analysed by GC.

[b] In an inert atmosphere, a 100 mL Shlenk bottle was a charged with diphenylamine (0.846 g, 5.0 mmol), 4-chloroanisole (0.784 g, 5.5 mmol) and 9 mL of xylene. Cooled to 5° C. by ice, 1.70 mL CH$_{3}$MgCl (3.0M solution in THF, 5.1 mmol) was added dropwise about 10 min. Added mixture solution of ligand, Pd(II), 0.26 mL dodecane, xylene and the reaction solution was heated to 145° C. The organic phase was analysed by GC.

Example 39,40

TABLE 2

The aminations of 4-Chlorotoluene with Diphenylamine; ZTPhos(example-14) as the ligand [a]

| Example | Pd Source (mol %) | P:Pd | Time (h) | Yield (%) |
|---|---|---|---|---|
| 39 | [PdCl(π-allyl)]$_{2}$ (0.5) | 2:1 | 6 | 90 |
| 40 | Pd(OAc)$_{2}$ (1.0) | 2:1 | 6 | 66 |

ZTPhos:

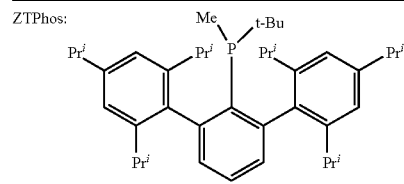

[a] In glove box, a mixture of aryl halide (1.1 mmol), diphenylamine(1.0 mmol), dodecane (130 uL, 0.57 mmol), NaOtBu (115 mg, 1.2 mmol), moderate of the ligand, Pd Source and 2 mL of toluene was taken in pressure tubing and heated at 100° C. The organic phase was analysed by GC.

Example 41

TABLE 3

The effect of ligand in the Suzuki reaction of 2-Bromotoluene with PhB(OH)$_2$[a]

| Example | ligand | Catalyst (mol %) | Yield (%) |
|---|---|---|---|
| 41 | XTPhos | 0.1 | 99 |
| literature data[b] | DmpPMe$_2$[c] | 1.0 | 91 |

[a]In glove box, a mixture of aryl halide (1.0 mmol), PhB(OH)$_2$ (1.5 mmol), dodecane (130 uL, 0.57 mmol), CsF (3.0 mmol), moderate of the ligand, Pd Source (P:Pd = 1:1) and 2 mL of dioxane was taken in pressure tubing and heated at 100° C. The organic phase was analyzed by GC.
[b]R.C. Smith, et al., Tetrahedron Letters 2004, 45, 8327-8330.
[c]DmpPMe$_2$:

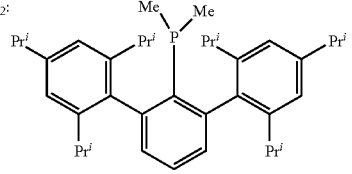

Example 42, 43

TABLE 4

The effect of ligand and it's complex in the aminations of 4-Chlorotoluene with carbazole[a]

| Example | Base | Tem (° C.) | Solvent | Pd Source (mol %) | P:Pd | Ligand | Time (h) | Yield (%) |
|---|---|---|---|---|---|---|---|---|
| 42 | NaO$^t$Bu | 100 | toluene | [PdCl(π-allyl)]$_2$ (0.5) | 2:1 | XTPhos | 3 | 92 |
| 43 | NaO$^t$Bu | 100 | toluene | [(XTPhos)(all)PdCl] (0.5) | — | — | 6 | 98 |
| literature data[b] | NaO$^t$Bu | 120 | xylene | [PdCl(π-allyl)]$_2$ (0.5) | 2:1 | cBRIDP[c] | 3 | 95 |

[a]In glove box, a mixture of aryl halide (1.1 mmol), carbazole (1.0 mmol), dodecane (130 uL, 0.57 mmol), NaOtBu (115 mg, 1.2 mmol), moderate of the ligand, Pd Source and 2 mL of toluene was taken in pressure tubing and heated at 100° C. The organic phase was analysed by GC.
[b]Ken Suzuki, et al., Adv. Synth. Catal. 2008, 350, 652-656.
[c]cBRIDP:

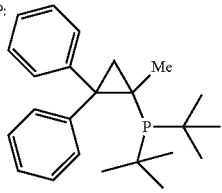

Example 44

TABLE 5

The effect of ligand in the aminations of 4-Chlorotoluene with morpholine[a]

| Example | Base | Tem. (° C.) | Solvent | Pd Source (mol %) | P:Pd | Ligand | Time (h) | Yield (%) |
|---|---|---|---|---|---|---|---|---|
| 44 | NaO$^t$Bu | 100° C. | toluene | Pd(OAc)$_2$ (1.0) | 2:1 | ZTPhos | 1 | 97 |
| literature data[b] | NaO$^t$Bu | reflux | toluene | Pd(OAc)$_2$ (2.5) | 2:1 | 8b-S[c] | 12 | 83 |

ZTPhos:

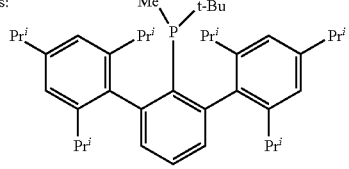

[a]In glove box, a mixture of aryl halide (1.0 mmol), morpholine (1.5 mmol), dodecane (130 uL, 0.57 mmol), NaOtBu (115 mg, 1.2 mmol), moderate of the ligand, Pd Source and 2 mL of toluene was taken in pressure tubing and heated at 100° C. The organic phase was analyzed by GC.
[b]Azusa Kondon, et al., J. Am. Chem. Soc. 2007, 129, 6996-6997.
[c]8b-S:

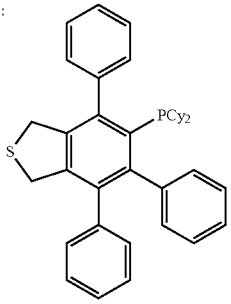

Example 45

TABLE 6

The effect of ligand in the Suzuki reaction of 1,3-dimethoxy-4,6-dibromobenzene with PhB(OH)$_2$, HTPhos(example-8) as the ligand[a]

| Example | Pd Source (mol %) | ligand | P:Pd | Time (h) | yield (%) |
|---|---|---|---|---|---|
| 45 | Pd(OAc)$_2$ (1.0) | HTPhos | 2:1 | 12 | 76 |
| literature data[b] | Pd(OAc)$_2$ (1.0) | SPhos[c] | 2:1 | 12 | 69 |

HTPhos:

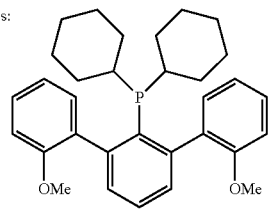

[a]In glove box, a mixture of aryl halide (1.0 mmol), PhB(OH)$_2$ (1.5 mmol), dodecane (130 uL, 0.57 mmol), K$_3$PO$_4$ (3.0 mmol), moderate of the ligand, Pd Source and 2 mL of toluene was taken in pressure tubing and heated at 100° C. The organic phase was analyzed by GC.
[b]Stephen L. Buchwald, et al., Angew. Chem. Int. Ed. 2004, 43, 1871-1876.

TABLE 6-continued

The effect of ligand in the Suzuki reaction of 1,3-dimethoxy-4,6-dibromobenzene with PhB(OH)$_2$, HTPhos(example-8) as the ligand[a]

[c]SPhos:

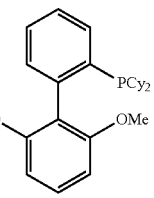

The invention claimed is:
1. Triaryl phosphine ligands are elected from the group consisting of the following specific phosphine compounds:
[2,6-Bis(2,6-dimethylphenyl)phenyl]-diphenylphosphine;
[2,6-Bis(2,6-dimethylphenyl)phenyl]-dicyclohexylphosphine;
[2,6-Bis(2,6-dimethylphenyl)phenyl]-cyclohoxyl-2-thienylphosphine;
[2,6-Bis(2,6-dimethylphenyl)phenyl]-tert-butyl-2-furylphosphine;
[2,6-Bis(2,4,6-trimethylphenyl)phenyl]-[2-dimethylaminophenyl]-phenylphosphine;
[2,6-Bis(2,4,6-trimethylphenyl)phenyl]-[2-dimethylaminophenyl]-cyclohexylphosphine;
[2,6-Bis(2,4,6-trimethylphenyl)phenyl]-[2-dimethylaminophenyl]-tert-butylphosphine;
[2,6-Bis(2,6-diisopropylphenyl)phenyl]-dicyclohexylphosphine;
[2,6-Bis(2,6-diisopropylphenyl)phenyl]-phenyl-cyclohexylphosphine;
[2,6-Bis(2,6-diisopropylphenyl)phenyl]-methyl-tert-butylphosphine;
[2,6-Bis(2,6-diisopropylphenyl)phenyl]-phenyl-isopropylphosphine;
[2,6-Bis(2,6-diisopropylphenyl)phenyl]-[2',6'-dimethyl-2-biphenyl]-methylphosphine;
[2,6-Bis(2,6-diisopropylphenyl)phenyl]-[2',6'-dimethoxy-2-biphenyl]-methylphosphine;
[2,6-Bis(2,6-diisopropylphenyl)phenyl]-[2',6'-dimethoxy-2-biphenyl]-cyclohexylphosphine;
[2,6-Bis(2,6-diisopropylphenyl)phenyl]-[2',6'-diisopropyl-2-biphenyl]-cyclohexylphosphine;
[2,6-Bis(2,4,6-triisopropylphenyl)phenyl]-dicyclohexylphosphine;
[2,6-Bis(2,4,6-triisopropylphenyl)phenyl]-phenyl-cyclohexylphosphine;
[2,6-Bis(2,4,6-triisopropylphenyl)phenyl]-methyl-tert-butylphosphine;
[2,6-Bis(2,4,6-triisopropylphenyl)phenyl]-cyclohexyl-isopropylphosphine;
[2,6-Bis(2,4,6-triisopropylphenyl)phenyl]-[2',6'-dimethyl-2-biphenyl]-n-butylphosphine;
[2,6-Bis(2,4,6-triisopropylphenyl)phenyl]-[2',6'-dimethoxy-2-biphenyl]-methylphosphine;
[2,6-Bis(2,4,6-triisopropylphenyl)phenyl]-[2',6'-dimethoxy-2-biphenyl]-cyclohexylphosphine;
[2,6-Bis(2,4,6-triisopropylphenyl)phenyl]-[2',6'-diisopropyl-2-biphenyl]-tert-butylphosphine.

* * * * *